United States Patent [19]

Masuzawa et al.

[11] Patent Number: 5,591,911
[45] Date of Patent: Jan. 7, 1997

[54] ULTRASOUND SIGNAL PROCESSOR

[75] Inventors: Hiroshi Masuzawa, Hachioji; Ryuuichi Shinomura, Higashimatsuyama; Kageyoshi Katakura, Tokyo, all of Japan

[73] Assignee: Hitachi Medical Corporation, Tokyo, Japan

[21] Appl. No.: 497,803

[22] Filed: Jul. 3, 1995

[30] Foreign Application Priority Data

Jul. 5, 1994 [JP] Japan .................. 6-153397

[51] Int. Cl.⁶ .................. G01N 29/06; G01N 29/10
[52] U.S. Cl. .................. 73/602; 128/661.01; 367/88; 364/413.25; 364/724.13; 73/626
[58] Field of Search ............... 128/661.01, 660.01, 128/660.07; 73/625, 626, 606, 602; 364/724.16, 413.25, 724.13; 367/88, 7

[56] References Cited

U.S. PATENT DOCUMENTS

| 5,187,687 | 2/1993 | Burckhardt et al. | 128/660.01 |
| 5,231,573 | 7/1993 | Takamizawa | 364/413.25 |
| 5,261,281 | 11/1993 | Katakura et al. | 73/626 |
| 5,299,576 | 4/1994 | Shiba | 128/660.07 |
| 5,349,960 | 9/1994 | Gondo | 128/661.09 |
| 5,477,479 | 12/1995 | Ochi | 364/724.16 |
| 5,515,727 | 5/1996 | Miwa et al. | 73/602 |

FOREIGN PATENT DOCUMENTS 5-211223  9/1977  Japan .

Primary Examiner—Hezron E. Williams
Assistant Examiner—Rose M. Finley
Attorney, Agent, or Firm—Antonelli, Terry, Stout & Kraus

[57] ABSTRACT

An ultrasound signal processor for receiving an ultrasound signal from a testing body by a plurality of electro-magnetic transducer elements and processing a plurality of received signals to obtain information of the interior of the testing body is provided with analog-digital converters for sampling at least two of received analog signals, multipliers for multiplying the outputs of the analog-digital converters by first complex digital reference signals, first low-pass filters for limiting the signal bands of the outputs of the multipliers, first complex multipliers for multiplying the outputs of the first low-pass filters by second complex digital reference signals, adders for performing the addition of the outputs of the first complex multipliers for real signals and the addition thereof for imaginary signals, memory devices for storing the outputs of the adders, second complex multipliers for multiplying signals read from the memory devices by third complex digital reference signals, and second low-pass filters for limiting the signal bands of the outputs of the second complex multipliers.

10 Claims, 18 Drawing Sheets

ULTRASOUND SIGNAL PROCESSOR

BACKGROUND OF THE INVENTION

The present invention relates to an ultrasound signal processor used in an ultrasound imaging system such as an ultrasound diagnostic system or ultrasound non-destructive testing system, and more particularly to an ultrasound signal processor for processing received ultrasound signals on the basis of digital beamforming.

In the conventional ultrasound imaging system, an ultrasound pulse signal is transmitted into a testing body or patient and an echo signal from a location having a different specific acoustic impedance (or a reflector) is received to obtain a sectional image or the like. In this case, the reception is made in such a manner that different delay times are given to the respective channels of a group of parallel received signals on the basis of the assumption of a transmission time of sound wave between a specified position in the testing body and receiving elements (or electro-acoustic transducer elements) to make phase matching and an echo signal from a reflector is obtained by use of interference caused by coherent signal addition.

In general, if the numbers of parallel received signals is large, a larger receiving aperture can be set, thereby making it possible to improve the resolution for a focal point on receiving. For this purpose is used an synthetic aperture method in which an ultrasound transmitting and receiving process is performed plural times to make the addition while moving the position of a receiving aperture for the same focal point (see, for example, JP-A-52-112223). However, in the case where a reflector in a testing body is in activity or motion (particularly in the case of an ultrasound diagnostic system or the like), there is problem that the correct addition of coherent or in-phase signals is not possible since the position of the reflector in the testing body moves in a period of time when the ultrasound transmitting and receiving process is performed plural times.

As a broad-band transmission system in the research field of communication, there is widely known a technique in which channels are formed by dividing a signal into frequency bands and a plurality of signals are transmitted in a single transmission route in a band limited and compressed form by use of a modulation and demodulation technique based on the frequency shift of a band. Particularly in the transmission of sound or voice signals, there is known a single side band (SSB) transmission system.

SUMMARY OF THE INVENTION

In order to avoid the above problem, it is required that all received signals to be subjected to beamforming (or coherent addition) at a time should be certainly subjected to simultaneous parallel reception so that the signal values are taken in. For that purpose, memory devices are provided for storing parallel received signals for respective receiving channels and a processing for read-out from the memory device is performed in accordance with the performance of parallel processing of beamforming circuits. For example, in the case where received signals two times in number as large as the performance of parallel processing of the beamforming circuits are to be processed, a circuit for simultaneous reception and the memory device for storing the signal values are provided with a doubled capacity and the beamforming circuit is operated by a sequential batch procedure performed twice to obtain a final output of addition. This construction requires a memory device which stores the total length of received signals (or the whole of received signals) subjected to simultaneous reception at a time and has a capacity equivalent to the number of received signals.

When comparing the beamforming process of received ultrasound signals with the transmission processing of sound or voice signals, there are some points remarkably different from the transmission of voice signals. Namely, for the beamforming of received ultrasound signals, it is necessary to strictly maintain the phase information of the signal. Also, the frequency characteristic of the received signal changes depending on the position of a reflector in a testing body. There is performed a multi-beamforming process in which the same time series signal is read at different phase conditions and is processed plural times.

The above-mentioned prior art has the following problems. Namely, in order to increase the number of received signals capable of being subjected to simultaneous beamforming, there are needed not only means for simultaneously acquiring received signals, for example, analog-digital converters and demodulating circuits but also a memory device for storing the whole of received signals (or the total length of received signals) which are received once. However, when seeing the scale of a system construction, since the capacity of the memory device, for example, random access memory (RAM) occupies a large relative importance, the separate provision of such a memory device makes no practical difference from the case where the performance of parallel processing of the beamforming circuits is merely increased by the number of received signals.

Therefore, the beamforming process based on the sequential batch procedure cannot be regarded as being an advantageous method for the enlargement of a receiving aperture and has a poor practicability.

On the other hand, in the above-mentioned transmission system in the research field of communication, the technique of compressing signals on a frequency axis while limiting band is widely known but there are not disclosed a processing and construction assuming that the phase of a received signal should be strictly maintained and a technique in which consideration is given to the conditions peculiar to an ultrasound beamformer including the plural use of the same signal portion as in the case where a multi-beam (or parallel beam) is used.

An object of the present invention made for solving the above problems of the prior art is to provide an ultrasound signal processor in which a plurality of parallel inputted ultrasound signals are compressed on a frequency axis and are demodulated taking the plural use of the same signal portion into consideration.

An ultrasound signal processor of the present invention for compressing a plurality of parallel inputted ultrasound signals on a frequency axis and demodulating the compressed signals taking the plural use of the same signal portion into consideration is characterized by comprising analog-digital converters for sampling received ultrasound signals, multipliers for performing frequency shift by first complex digital reference signals, a first low-pass filter for limiting signal band, first complex multipliers for performing frequency shift by second complex digital reference signals, adders for performing the addition of the outputs of the first complex multipliers for real signals and the addition thereof for imaginary signals, a pair of memory devices for storing the outputs of the adders, second complex multipliers for frequency-shifting the received signals read from the memory devices by third complex digital reference signals, and a second low-pass filter for limiting the bands of the frequency-shifted signals.

The above object of the present invention is attained by the following construction.

In a first construction of the present invention, an ultrasound beamformer comprises a group of analog-digital converters for sampling received ultrasound signals, a group of multipliers for performing frequency shift by a group of first complex digital reference signals, a first low-pass filter for limiting signal band, a group of first complex multipliers for performing frequency shift by a group of second complex digital reference signals, adders for performing the addition of the outputs of the first complex multipliers for real signals and the addition thereof for imaginary signals, a pair of memory devices for storing the outputs of the adders, a group of second complex multipliers for frequency-shifting the received signals read from the memory devices by a group of third complex digital reference signals, and a second low-pass filter for limiting the bands of the frequency-shifted signals.

A second construction of the present invention is such that in the first construction, the number of parallel-arranged complex multipliers in each of the first and second complex multiplier groups is less than the number of parallel-arranged analog-digital converters by one.

A third construction of the present invention is such that in the first construction, there are additionally provided a group of selectors for signal selection so that the first complex multiplier acts for the function of the second complex multiplier to omit the second complex multiplier and the first low-pass filter acts for the function of the second low-pass filter to omit the second low-pass filter.

A fourth construction of the present invention is such that in the first construction, there are additionally provided a sampler for enabling a time sharing procedure in a construction succeeding the memory devices and a group of second low-pass filters corresponding to the total of parallel process increased due to the time sharing procedure, and there are provided selectors for outputting the outputs of the second low-pass filters in a time sharing manner.

A fifth construction of the present invention is such that in the fourth construction, a plurality of such samplers for enabling the time sharing procedure are provided and the filters in the group of second low-pass filters are parallel-arranged corresponding to the plurality of samplers, and there is provided another adder for partially adding the outputs of the second low-pass filters.

A sixth construction of the present invention is such that in the first construction, the whole of the construction of a portion for performing the frequency shift and addition of the parallel received signals is formed by analog circuits and a signal after addition is sampled by an analog-digital converter.

With the above construction, the system of the present invention can realize the following operation.

With the first construction of the present invention, the received analog ultrasound signals are sampled by the analog-digital converters. The succeeding multipliers and first low-pass filter perform frequency shift (or demodulation) by the first complex digital reference signals. The first complex digital reference signals may be set taking a phase difference between a sampling timing pulse signal and the carrier of the received signal into consideration. The first complex multipliers perform frequency shift (or modulation) by the second complex digital reference signals. Thereby, different received signals are frequency-shifted to bands having different center frequencies. The addition of the outputs of the first complex multipliers for real signals and the addition of the outputs thereof for imaginary signals are made by the pair of adders. The outputs of the adders are stored into the pair of memory devices. The received signals read from the memory devices are frequency-shifted (or demodulated) by the third complex digital reference signals to bands centering around a DC position. The second low-pass filter for limiting the bands of the frequency-shifted signals ultimately outputs a complex signal having a single band. With the above construction taken as one beamformer unit, a plurality of such beamformer units are parallel-arranged to form a beamformer. Each beamformer unit provides a pair of real and imaginary outputs. Moreover, the output signals from the respective beamformer units may be added simultaneously or by a sequential bath procedure for each of the real and imaginary outputs.

One of frequency bands used for storage in the memory device in a compressed form may be a band centering around the DC position. Therefore, in the second construction of the present invention, there are omitted that one of the first complex multipliers which corresponds to the modulation resulting in the storage into the memory device with the DC-shifted carrier of the received signal maintained and that one of the second complex multipliers which corresponds to the demodulation of a band centering around the DC position.

With the third construction of the present invention, the received signals stored in the memory devices having different bands can be read through a batch procedure, thereby attaining the simplification of the construction.

With the fourth construction of the present invention, there can be realized an operation in which the received signals stored in the memory device having different frequency bands are read through a time sharing procedure with alternating band frequencies and an operation in which the received signal stored in the memory device having the same frequency band is read through a time sharing procedure with alternating beamforming conditions. Thus, a part or the whole of a batch procedure is replaced by the time sharing procedure, thereby enabling a high-speed beamforming process.

With the fifth construction of the present invention, it is possible to perform a beamforming processes for signals which are read from the same received signal band under different beamforming conditions. Simultaneously, it is possible to perform beamforming processes which add signals, are compressed to different signal bands. With such a beamforming process, the number of time sharing outputs from the beamformer unit can be reduced. In the case where the speed of time sharing read-out from the memory device is higher than a sampling period of the received signal, the number of time sharing procedures can be reduced to the number of beamforming conditions.

With the sixth construction of the present invention in which the whole of a portion of the first construction for performing the frequency shift and addition of the parallel received signals is replaced by analog circuits and a signal after addition is sampled by an analog-digital converter, the number of analog-digital converters required for respective parallel receiving channels can be reduced to two, thereby enabling the considerable reduction of the number of signal lines and the reduction of the constructing cost when the circuit construction is implemented.

It is particularly important that with the first to sixth constructions, the time (or phase) precision at the sampling period of the analog-digital converter is maintained as the time precision of the received signal as it is.

As explained in detail in the foregoing, the present invention provides a remarkable effect that an ultrasound signal processor can be realized in which a plurality of parallel inputted ultrasound signals are compressed on a frequency axis and are demodulated taking the plural use of the same signal portion into consideration.

More particularly, there is obtained an effect that an ability of storing signals while simultaneously receiving them through an ultrasound transmitting and receiving process performed once can be improved greatly. Namely, though the prior art requires the provision of memory devices parallel-arranged for the respective received signals, the present invention enables the storage in a single memory device using a signal band compressing procedure, thereby attaining the reduction in circuit scale. Further, a beamforming process under different conditions can be realized using a time sharing procedure, thereby enabling a high-speed imaging.

DESCRIPTION OF THE PREFERRED EMBODIMENTS

Figure 1:
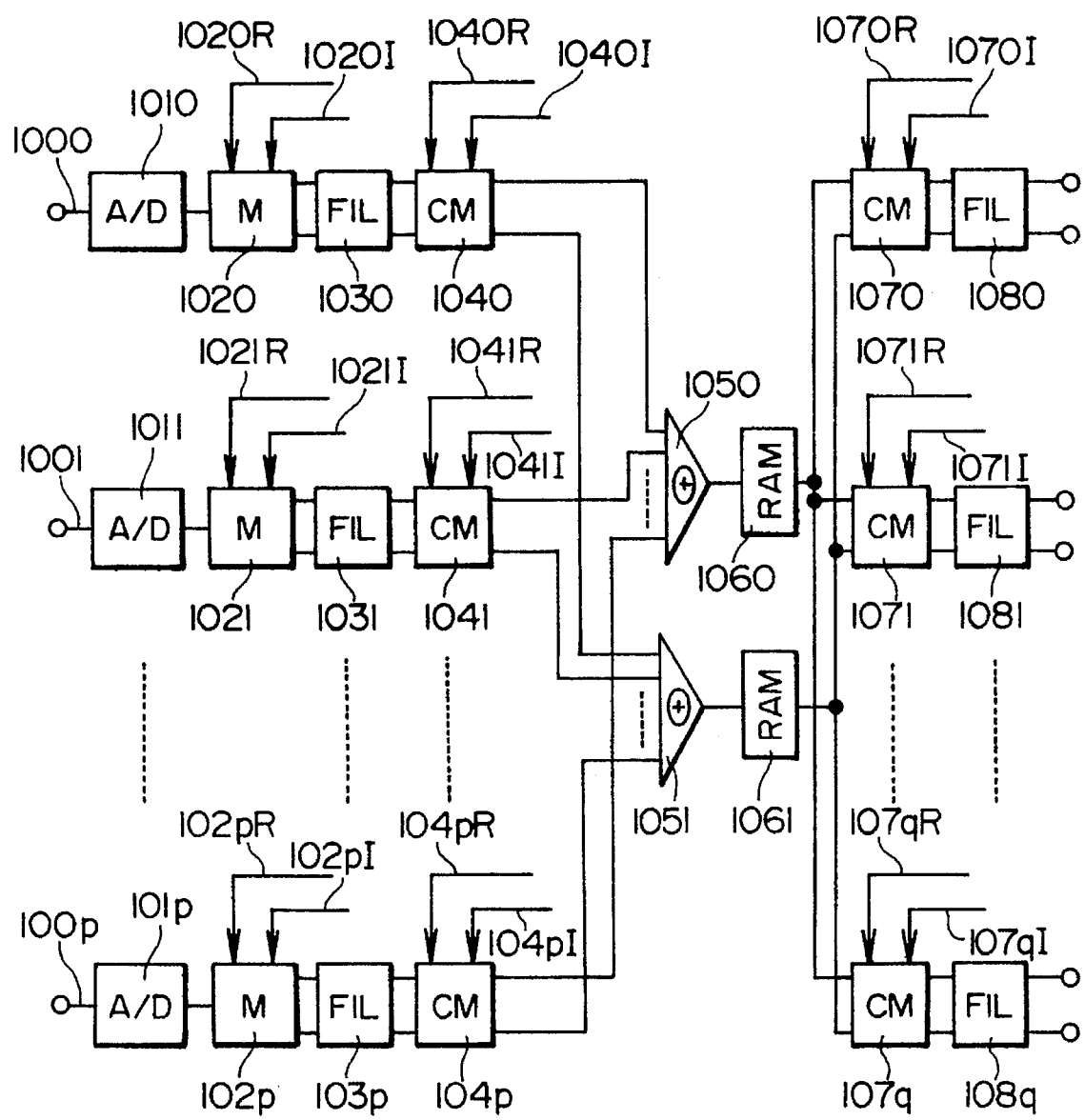
FIG. 1 is a block diagram in the case where an ultrasound signal processor according to an embodiment of the present invention is formed by digital circuits.

Embodiments of the present invention will now be described in detail on the basis of the accompanying drawing.
(Embodiment 1)
A first embodiment of the present invention will be explained by use of FIG. 1.

Received ultrasound signals 1000, 1001, - - - and 100$p$ are inputted to multipliers (M) 1020, 1021, - - - and 102$p$ through analog-digital (A/D) converters 1010, 1011, - - - and 101$p$. The multipliers (M) 1020, 1021, - - - and 102$p$ multiplies the outputs of the analog-digital (A/D) converters 1010, 1011, - - - and 101$p$ by reference sine signals 1020R, 1021R, - - - and 102pR and reference cosine signals 1020I, 1021I, - - - and 102pI. The outputs of the multipliers (M) 1020, 1021, - - - and 102$p$ are inputted to low-pass filters (FIL) 1030, 1031, - - - and 103$p$. The outputs of the low-pass filters (FIL) 1030, 1031, - - - and 103$p$ are inputted to complex multipliers (CM) 1040, 1041, - - - and 104$p$.

The complex multipliers (CM) 1040, 1041, - - - and 104$p$ are also inputted with reference sine signals 1040R, 1041R, - - - and 104pR and reference cosine signals 1040I, 1041I, - - - and 104pI. The results of complex multiplication by the complex multipliers are inputted to adders 1050 and 1051. The outputs of adders 1050 and 1051 are stored into memory devices 1060 and 1061 each of which may be a random access memories (RAM).

Outputs read from the memory devices (RAM) 1060 and 1061 at a predetermined instant of time are inputted to complex multipliers (CM) 1070, 1071, - - - and 107$q$.

The complex multipliers (CM) 1070, 1071, - - - and 107$q$ are also inputted with reference sine signals 1070R, 1071R, - - - and 107qR and reference cosine signals 1070I, 1071I, - - - and 107qI. The results of complex multiplication by the complex multipliers are inputted to low-pass filters (FIL) 1080, 1081, - - - and 108$q$. The outputs of the low-pass filters (FIL) 1080, 1081, - - - and 108$q$ are ultimately converted into an image signal by the succeeding signal processing circuit (not shown).

Next, the functions of the respective parts will be explained in sequence.

Received ultrasound signals 1000, 1001, - - - and 100$p$ are inputted to the analog-digital (A/D) converters 1010, 1011, - - - and 101$p$ and quantized thereby in accordance with a predetermined sampling period. In the construction shown in FIG. 1, only the inputs 1000, 1001, - - - and 100$p$ are analog signals. The received signals converted into digital signals are inputted to the multipliers (M) 1020, 1021, - - - and 102*p*.

In the multipliers (M) 1020, 1021, - - - and 102*p*, the received signals converted to digital signals are multiplied by reference sine signals 1020R, 1021R, - - - and 102pR and reference cosine signals 1020I, 1021I, - - - and 102pI which are orthogonal to each other. Thereby, a band of the received signal is frequency-shifted. The frequency of the reference signal is selected to be the center frequency of the received signal. The reference sine signals may have the same phase or may subjected to phase rotation in accordance with the purpose so that they have different phases. This holds for the reference cosine signals.

In the multipliers (M) 1020, 1021, - - - and 102*p*, the group of received signals are multiplied by the sine signals and the cosine signals to generate two signal groups. In the construction shown in FIG. 1, the succeeding signal processing is performed by two orthogonal systems of digital signal processings. These are handled as a pair of complex signals which represent a real (or in-phase) signal part and an imaginary (or quadrature) signal part, respectively.

The low-pass filters (FIL) 1030, 1031, - - - and 103*p* perform the filtering of signal while leaving a signal band shifted to the vicinity of the DC position of a frequency spectrum through the complex frequency shift. Thereby, it is possible to sufficiently attenuate a signal band which is at a position corresponding to a frequency two times as high as the center frequency of the original signal band on the frequency spectrum. The outputs of the low-pass filters (FIL) 1030, 1031, - - - and 103*p* are inputted to the complex multipliers (CM) 1040, 1041, - - - and 104*p*.

The complex multipliers (CM) 1040, 1041, - - - and 104p are also inputted with reference sine signals 1040R, 1041R, - - - and 104pR and reference cosine signals 1040I, 1041I, - - - and 104pI to make complex multiplication so that the signal band in the vicinity of the DC position is shifted again to a position centering around a desired frequency. At this time, the signal bands moved by the complex multipliers (CM) 1040, 1041, - - - and 104*p* on the spectrum are made coincident with each other or are separated without overlapping, as required.

The frequency of the reference sine signals 1040R, 1041R, - - - and 104pR and the reference cosine signals 1040I, 1041I, - - - and 104pI inputted to the complex multipliers (CM) 1040, 1041, - - - and 104*p* can be selected to be, for example, 0, ±cB, ±2cB, ±3cB, and ±ncB, where the maximum width among all signal bands to be subjected to shifting is B, c is larger than 1.0 and n is an integer. The particular case of n=0 is equivalent to the case where no frequency shift is performed. This means that one complex multiplier is omitted so that an input is outputted as it is.

With the frequency shift, the original received signals have single-bands on the frequency spectrum and the respective frequency regions occupied by the received signals are different. Therefore, even if the addition is made, it is possible to avoid the interference of signal components. Since the outputs of the complex multipliers (CM) 1040, 1041, - - - and 104*p* for real signals and the outputs thereof for imaginary signals are added by the adders 1050 and 1051, respectively, the original group of plural received signals are compressed into a single complex signal.

The absolute frequency value of the band of the output signal from the complex multiplier (CM) 1040, 1041, - - - or 104*p* should be equal to or lower that one half of the sampling frequency of the analog-digital (A/D) converters 1010, 1011, - - - and 101*p*.

The outputs of the adders 1050 and 1051 are stored into the memory devices (RAM) 1060 and 1061. All the above-mentioned series of received signals are stored into the memory devices (RAM) 1060 and 1061 after the above-mentioned complex frequency shift and band compression. The read-out of compressed signals from the memory devices (RAM) 1060 and 1061 is performed at a predetermined instant of time in compliance with a required delay time.

The memory device may comprise a shift register, fast-in fast-out (FIFO) memory or the like in lieu of the above-mentioned random access memory (RAM).

The outputs read from the memory devices (RAM) 1060 and 1061 are inputted to the complex multipliers (CM) 1070, 1071, - - - and 107*q*. The complex multiplier (CM) 1070, 1071, - - - or 107*q* shifts the band of the compressed signal on the frequency axis. The frequency of a reference signal inputted to each complex multiplier (CM) is selected such that a desired band of the compressed signal is shifted to a band centering around the DC position so that a single signal band as desired is obtained after the passing through the succeeding low-pass filters (FIL) 1080, 1081, - - - or 108*q*.

The frequency of the reference sine signals 1070R, 1071R, - - - and 107qR and the reference cosine signals 1070I, 1071I, - - - and 107qI inputted to the complex multipliers (CM) 1070, 1071, - - - and 107*q* is equal to the sign-inverted version of either the frequency of the reference sine signals 1040R, 1041R, - - - and 104pR or the frequency of the reference cosine signals 1040I, 1041I, - - - and 104pI used at the time of band compression.

It is not required that the number q of signals to be parallel-processed after read-out from the memory devices (RAM) 1060 and 1061 should be equal to the total number p of received signals used at the time of band compression. Also, it is not required that the number q of signals to be parallel-processed after read-out should be equal to the total number of signal bands independently provided at the time of band compression. For example, in the case where the memory devices 1060 and 1061 are formed by RAM's and the number q of signals to be parallel-processed after read-out is made smaller than the total number of signal bands independently provided at the time of band compression, a series of operations performing the compression of the received signals, the storage of the compressed signals into the memory devices (RAM) 1060 and 1061 and the read-out of the stored signals with sequential delay can be followed by an operation of performing only the read-out from the memory devices 1060 and 1061 again. This is a procedure in which the received signals simultaneously compressed through a parallel processing are read by a batch procedure. On the other hand, in the case where the number q of signals to be parallel-processed after read-out is made larger than the total number of signal bands independently provided at the time of band compression, the read signals having the same band can be subjected to different complex signal processings.

The outputs of the low-pass filters (FIL) 1080, 1081, - - - and 108*q* are ultimately converted into an image signal by the succeeding signal processing circuit (not shown). The signal processing performed by the signal processing circuit (not shown) may include the addition of real signals and the addition of imaginary signals in all of the respective low-pass filter outputs or each of divisional groups of these outputs, the square sum and logarithmic amplitude compression of the real signals parts and those of the imaginary signals or a Doppler signal processing thereof, and so forth.

According to the above embodiment, there can be realized an ultrasound signal processor which is capable of compressing a plurality of parallel inputted ultrasound signals on a frequency axis and demodulating them with the plural use of the same signal portion being taken into consideration. (Embodiment 2)

Next, explanation will be made of an embodiment in which the construction shown in FIG. 1 is used for the enlargement of a receiving aperture in the form of a construction having the minimized total of parallel process.

First, the enlargement of the receiving aperture will be explained using FIG. 11.

Figure 11:
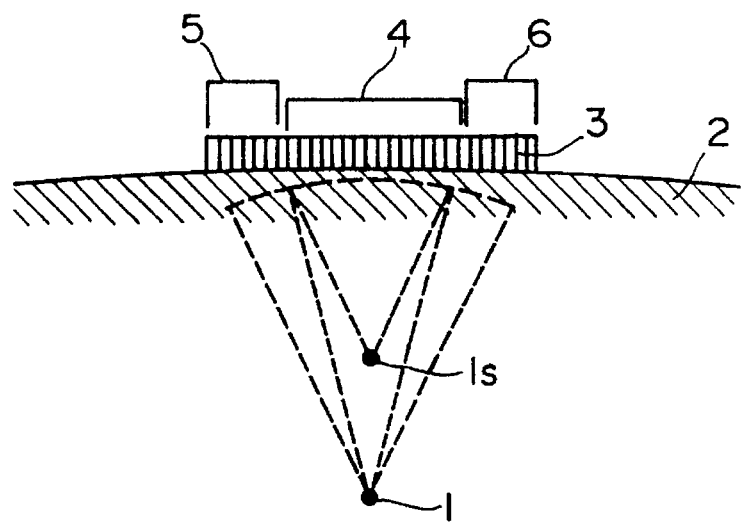
FIG. 11 is a diagram for explaining a beamforming process in the case where the imaging is performed with a receiving aperture being divided into a plurality of parts.

In FIG. 11, an echo signal from a receiving focal point 1 in a testing body or patient 2 is converted by an electroacoustic transducer 3 into an electric signal. The electroacoustic transducer 3 includes an array composed of a multiplicity of elements. In general, it is preferable that the elements are provided as large in number as possible and at an interval sufficiently small as compared with the wavelength of received sound waves. In the case where the number of those of elements provided in the system which can be parallel-subjected at a time to a signal processing such as delaying corresponds to only an aperture part 4, there can be considered a method in which reception data of aperture parts 5 and 6 is taken in simultaneously with the reception data of the aperture part 4 and is subjected to the signal processing such as delaying after the processing of the reception data of the aperture part 4.

Such an operation doubles a time required for the beamforming of received signals but can increase the number of elements capable of being subjected to a delay process at a time.

In order to realize the above method, it is generally necessary to store the reception data of the aperture parts 5 and 6 in separate memory devices. For example, a RAM or the like occupying a very large percentage in a circuit scale must be provided for each element. As a result, there is a problem that the resultant circuit scale becomes approximately equivalent to parallel arrangement for all receiving elements. However, if the band compression is performed using the construction shown in FIG. 1, the circuit scale can be reduced considerably since received signals of, for example, two channels are stored in a single RAM with band compressed. Particularly in the case where the electroacoustic converter 3 is formed by two-dimensionally arranged elements, the construction shown in FIG. 1 provides very effective means since a multiplicity of signals can be processed.

Figure 2:
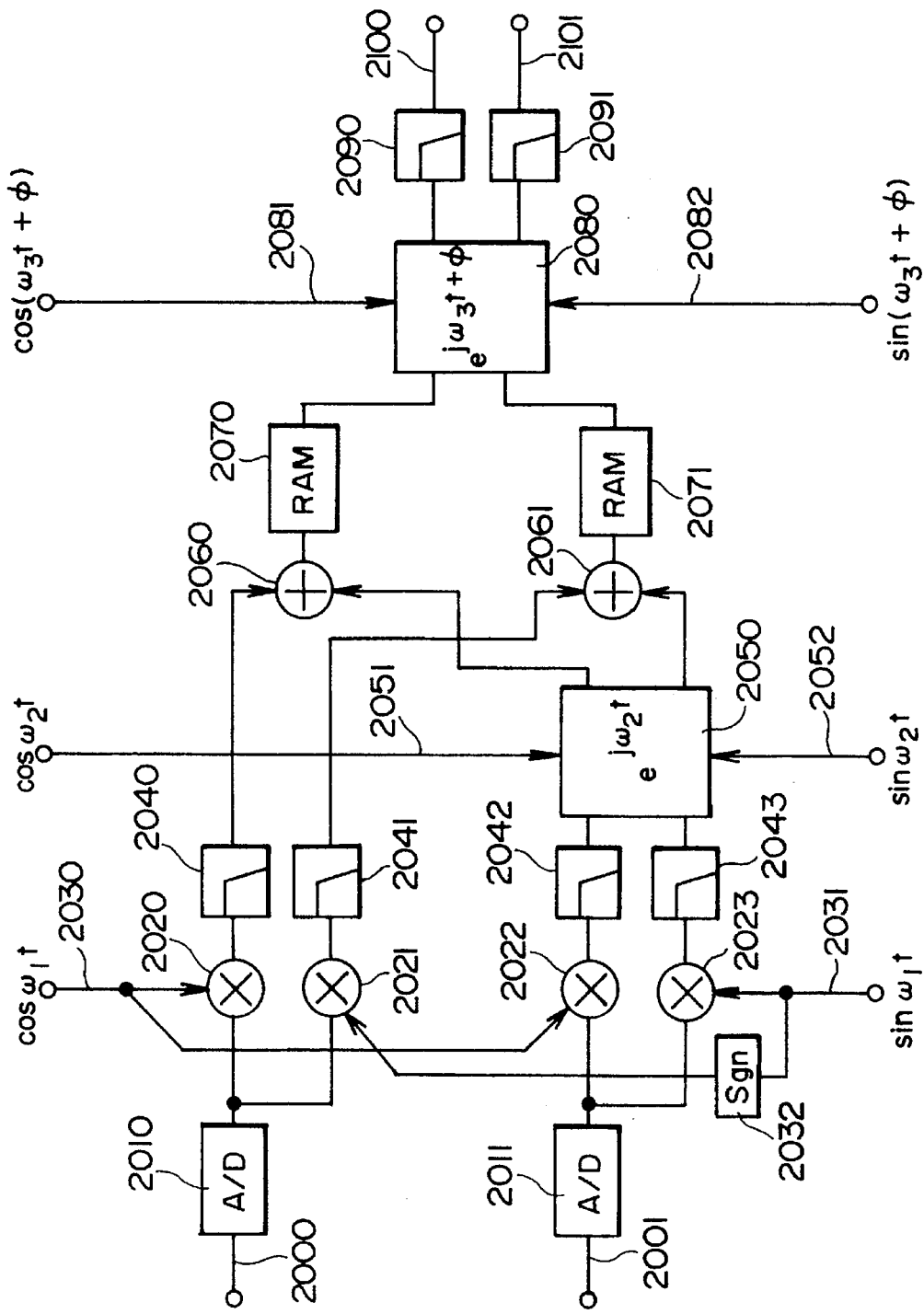
FIG. 2 is a block diagram in the case where the processor shown in FIG. 1 is constructed with two parallel inputs.

FIG. 2 shows an embodiment of a construction in which the beamforming for two channels of received signals with band compressed is performed. Received signal inputs 2000 and 2001 from different electroacoustic conversion elements (not shown) are supplied to analog-digital converters (A/D) 2010 and 2011, respectively. In FIG. 2, all signals excepting the received signal inputs 2000 and 2001 are digital signals. The sampled digital signals are inputted to multipliers 2020 to 2023 and are frequency-shifted thereby. The frequency-shifted signals are inputted to low-pass filters 2040 to 2043.

Reference signal inputs 2030 and 2031 of the multipliers 2020 to 2023 are sine and cosine signals having the same angular frequency $\omega_1$ but the sign of the reference sine signal 2031 is inverted by a sign inverter (Sgn) 2032 so that the shifting directions of the received signals 2000 and 2001 on the frequency spectrum are positive and negative. Namely, the received signal 2000 is subjected to a frequency shift $\exp(-j\omega_1 \cdot t)$ in the negative direction and the received signal 2001 is subjected to a frequency shift $\exp(j\omega_1 \cdot t)$ in the positive direction.

The multipliers 2020 to 2023 correspond to the multipliers 1020 to 102p in FIG. 1. Regarding the outputs of the low-pass filters 2040 to 2043, the outputs on the received signal 2000 side are inputted to adders 2060 and 2061 as they are, and those on the received signal 2001 side are inputted to a complex multiplier 2050. In the construction shown in FIG. 2, the center frequency of one of the two received signals is selected to be 0 and hence a complex multiplier for the one signal is omitted.

Reference signal inputs of the complex multiplier 2050 use a sine signal 2052 and a cosine signal 2051 which are orthogonal in phase and have an angular frequency $\omega_2$. The angular frequency $\omega_2$ is selected to be, for example, $\omega_2 = -\omega_1$ to cause a frequency shift $\exp(-j\omega_1 \cdot t)$ in the negative direction.

The outputs of the low-pass filters 2040 and 2041 and the outputs of the complex multiplier 2050 are inputted to the adders 2060 and 2061 which make the addition for real signals and the addition of imaginary signals, respectively.

The outputs of the adders 2060 and 2061 are written into memory devices (RAM) 2070 and 2071 for storage therein. The written signals are subjected to a delay process by reading them again and the read signals are frequency-shifted by a complex multiplier 2080. Also, a phase difference $\phi$ between the carrier of the received signal and the sampling timing pulse signal of the analog-digital converters 2010 and 2011 is corrected, as required.

In order to extract the signal band of the received signal 2001, sine and cosine signals 2081 and 2082 having an angular frequency $\omega_3$ are used as reference signal inputs to the complex multiplier 2080 and the angular frequency $\omega_3$ is selected to be $\omega_3 = \omega_1$. Thereby, the received signal 2001 is subjected again to an operation $\exp(j\omega_1 \cdot t + \phi)$ serving as both frequency shift in the positive direction and phase correction to turn the center frequency of the signal band of the received signal 2001 to 0 and is then filtered by the succeeding low-pass filters 2090 and 2091 to obtain single-band outputs 2100 and 2101.

In order to extract the signal band of the received signal 2000, the angular frequency $\omega_3$ of the reference signal inputs 2081 and 2082 to the complex multiplier 2080 is selected to be $\omega_3 = 0$. Thereby, the received signal 2002 is subjected to phase correction $\exp(j\phi)$ by the complex multiplier 2080 and is then filtered by the succeeding low-pass filters 2090 and 2091 to obtain single-band outputs 2100 and 2101.

Which of the bands of the received signals 2000 and 2001 is to be extracted is arbitrary in accordance with the purpose. Whichever signal band is to be extracted, the signal of that band is subjected to the delay process using the memory devices (RAM) 2070 and 2071, the frequency shift and phase correction process using the complex multiplier 2080 and the filtering by the low-pass filters 2090 and 2091. This procedure including the delay process using the memory devices (RAM) 2070 and 2071, the frequency shift and phase correction process using the complex multiplier 2080 and the filtering by the low-pass filters 2090 and 2091 is repeated.

More detailed explanation of the above signal processing will be made in conjunction with the shift on the frequency spectrum by use of FIGS. 5A to 5C, FIGS. 6A to 6D and FIGS. 7A to 7C.

Figure 5:
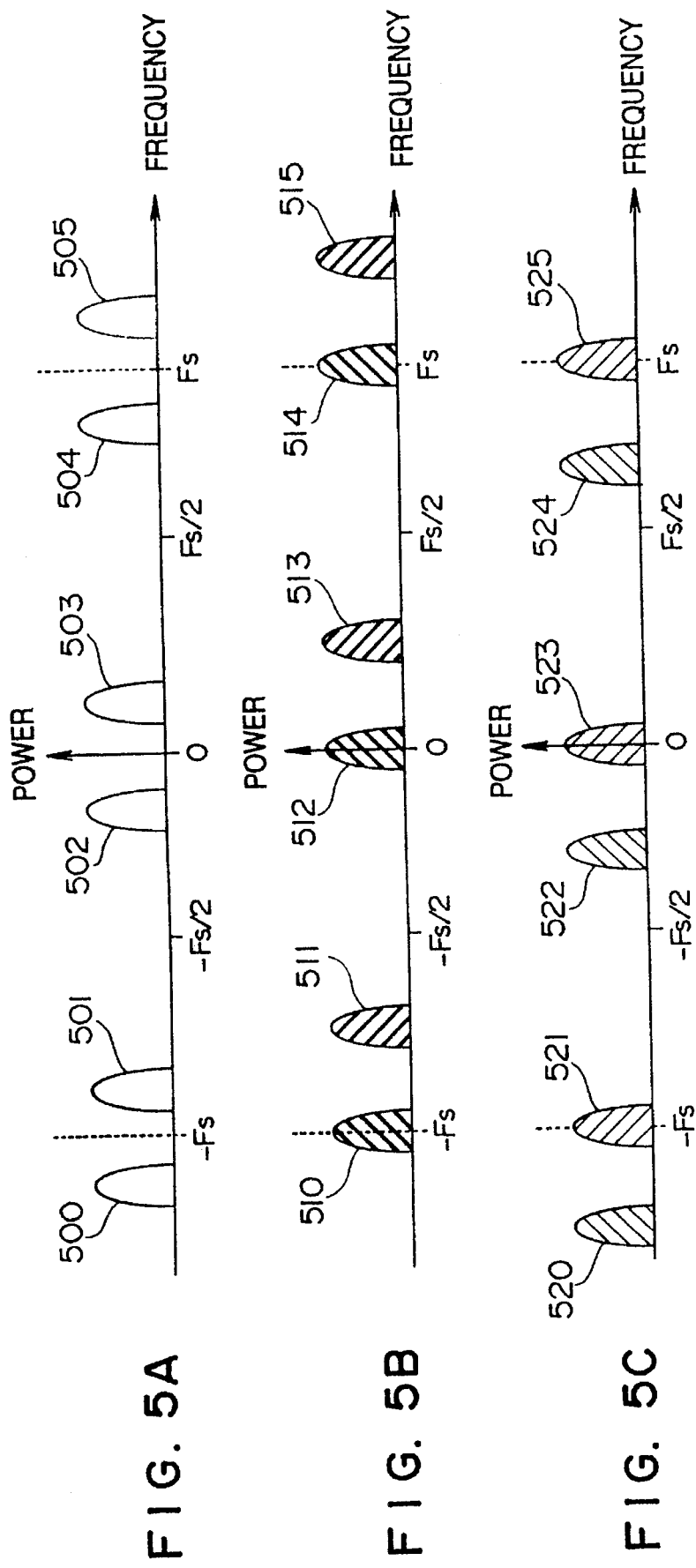
FIG. 5A is a diagram showing the spectrum of the output signal of an analog-digital converter shown in FIG. 2.
FIGS. 5B and 5C are diagrams showing the spectra of the output signals of multipliers shown in FIG. 2.

FIG. 5A shows the output signal of the analog-digital converter 2010 or 2011 shown in FIG. 2. In FIG. 5A, Fs is a sampling frequency. There exist alias bands 500 and 501, alias bands 504 and 505 and so forth of bands 502 and 503. FIG. 5B shows the outputs of the multipliers 2020 and 2021 of FIG. 2 handled as a pair of complex signals. In FIG. 5B, the bands 500 to 505 shown in FIG. 5A are all shifted in the positive frequency direction to bands 510 to 515. In order that each of the bands 510, 512 and 514 has a center frequency equal to integer times as high as the sampling frequency, the frequency of the reference signals 2030 and 2031 shown in FIG. 2 is made as coincident with the center frequency of the received signals 2000 and 2001 as possible.

Similarly, FIG. 5C shows the outputs of the multipliers 2022 and 2023 shown in FIG. 2. In FIG. 5C, the bands 500 to 505 shown in FIG. 5A are all shifted in the negative frequency direction to bands 520 to 525. Each of the bands 520, 522 and 524 has a center frequency which is integer times as high as the sampling frequency. FIGS. 6A to 6D show frequency spectra including the outputs of the low-pass filters 2040 to 2043, the complex multiplier 2050 and the adders 2060 and 2061 shown in FIG. 2.

Figure 6:
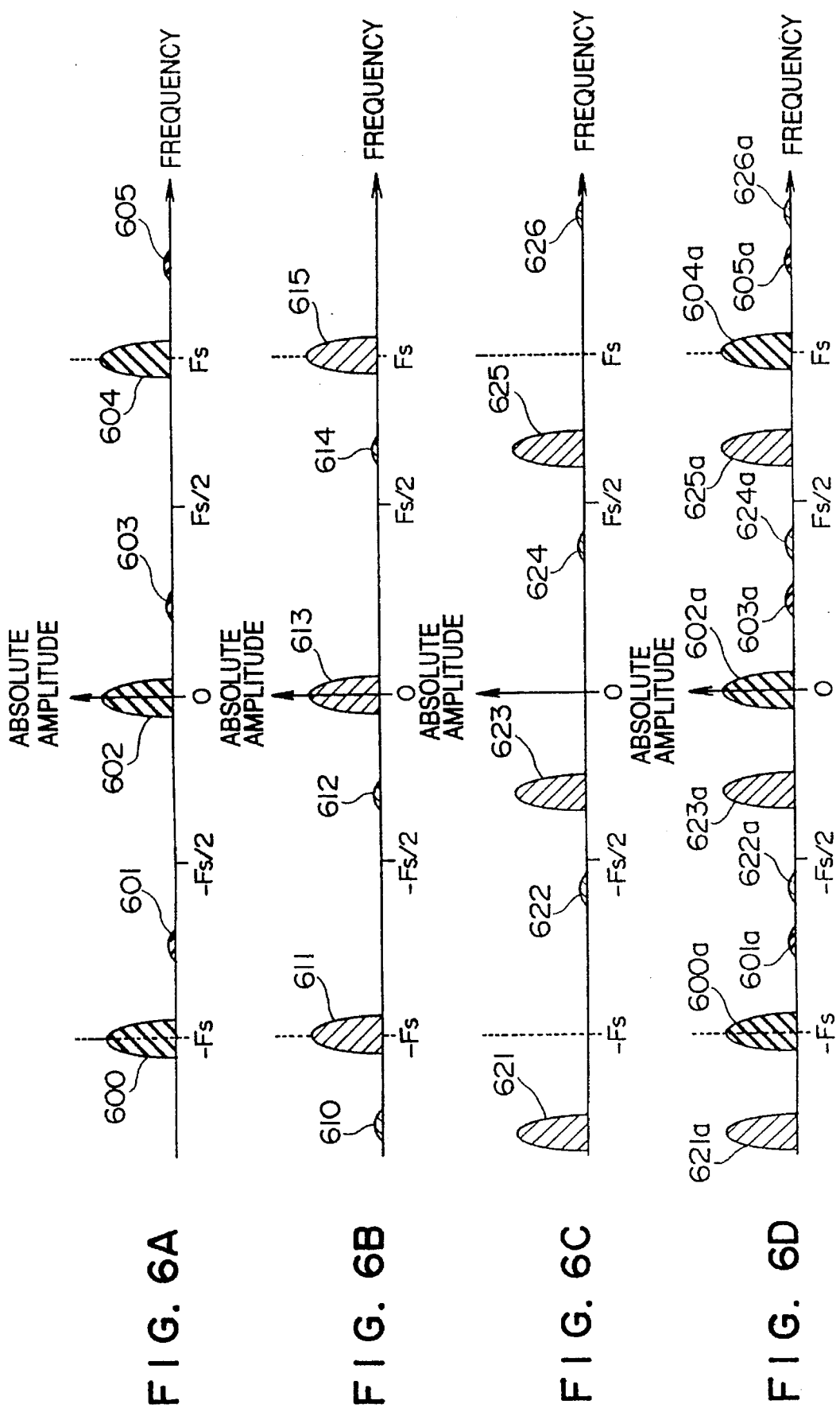
FIGS. 6A and 6B are diagrams showing the spectra of signals passed through low-pass filters shown in FIG. 2.
FIG. 6C is a diagram showing the spectrum of the output signal of a complex multiplier shown in FIG. 2.
FIG. 6D is a diagram showing the spectrum of the output signal of an adder shown in FIG. 2.

In FIG. 6A, the bands 511, 513 and 515 of FIG. 5B, which are the multiple frequency components, are attenuated by the low-pass filters so that they turn into bands 601, 603 and 605. The bands 510, 512 and 514 are passed as they are, resulting in bands 600, 602 and 604. In FIG. 6B, the bands 520, 522 and 524 of FIG. 5C, which are the multiple frequency components, are attenuated by the low-pass filters so that they turn into bands 610, 612 and 614. The bands 521, 523 and 525 are passed as they are, resulting in bands 611, 613 and 615.

FIG. 6C shows that the bands 611 to 615 of the spectrum shown in FIG. 6B are shifted in the negative frequency direction by the complex multiplier 2050 of FIG. 2 to bands 621 to 625. FIG. 6D shows the output of the adders 2060 or 2061 shown in FIG. 2. The spectrum shown in FIG. 6D corresponds to the superposition of the spectrum shown in FIG. 6A and the spectrum shown in FIG. 6C. The bands 600 to 605 shown in FIG. 6A turn into bands 600a to 605a, and the bands 621 to 626 shown in FIG. 6C turn into bands 621a to 626a. A signal having the spectrum shown in FIG. 6D is stored in the memory device (RAM) 2070 or 2071 and is then read for performing a delay process.

The delay process is performed for both the beamformed bands 602a and 623a and all the alias bands thereof at a time. This will now be explained.

In general, it does not necessarily follow that delay times to be given to signals (2000 and 2001 in FIG. 2) corresponding to the two bands 602a and 623a are the same. Therefore, in the construction shown in FIG. 2, the read-out from the memory devices (RAM) 2070 and 2071 should be performed separately two times. In the case where the received signal component originating from the signal 2000 shown in FIG. 2 is to be read, the signal of FIG. 6D read from the memory devices (RAM) 2070 and 2071 is multiplied in the complex multiplier 2080 of FIG. 2 by the reference signals 2081 and 2082 having the angular frequency $\omega_3$ of 0 and including only the phase $\phi$, and is then passed through the low-pass filters 2090 and 2091.

Figure 7:
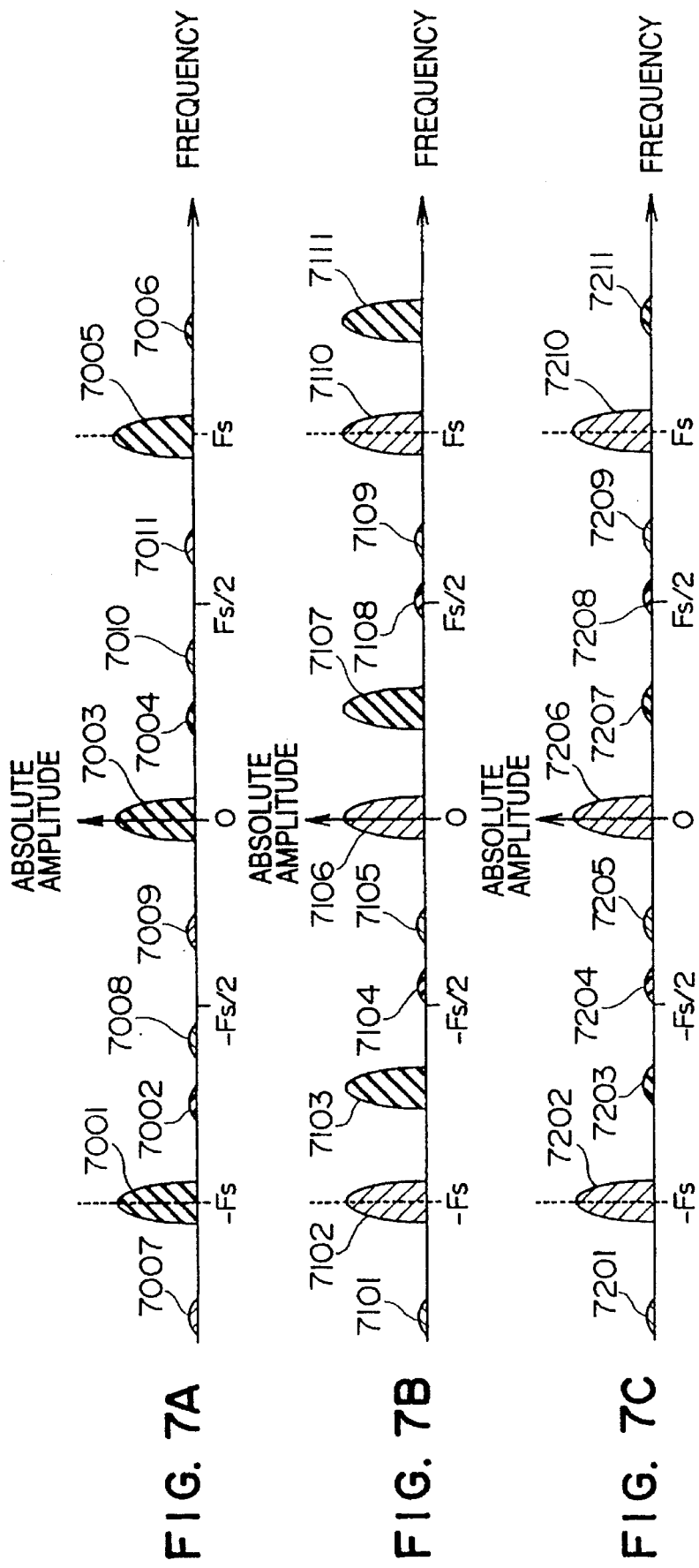
FIGS. 7A to 7C are spectral diagrams for explaining the demodulation from a compressed reception signal.

The passed spectrum is shown in FIG. 7A. The bands 621a to 626a, 601a, 603a and 605a shown in FIG. 6D are attenuated so that they turn into bands 7007 to 7011, 7002, 7004 and 7006 shown in FIG. 7A. The bands 600a, 602a and 604a shown in FIG. 6D are passed resulting in bands 7001, 7003 and 7005 shown in FIG. 7A.

Next, in the case where the received signal component originating from the signal 2001 shown in FIG. 2 is to be read, the signal of FIG. 6D read from the memory devices (RAM) 2070 and 2071 is multiplied in the complex multiplier 2080 of FIG. 2 by the reference signals 2081 and 2082 having the angular frequency $\omega_3$ equal to $\omega_1$ and including the phase $\phi$, and is then passed through the low-pass filters 2090 and 2091. The spectrum of the output signal of the complex multiplier 2080 is shown in FIG. 7B. This spectrum corresponds to a spectrum in which the bands shown in FIG. 6D are all shifted in the positive frequency direction by $\omega_1$ in angular frequency. With the succeeding low-pass filters 2090 and 2091, bands 7101, 7103 to 7105, 7107 to 7109 and 7111 shown in FIG. 7B are attenuated so that they turn into bands 7201, 7203 to 7025, 7207 to 7209 and 7211 shown FIG. 7C. Bands 7102, 7106 and 7110 are passed resulting in bands 7202, 7206 and 7210.

Figure 10:
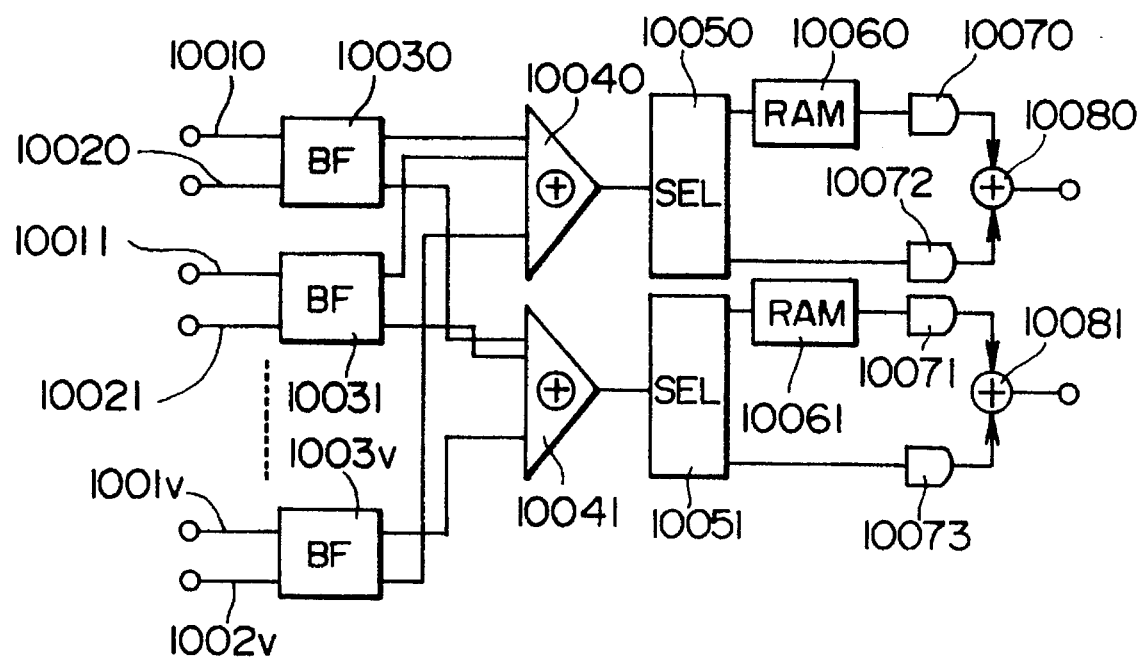
FIG. 10 is a block diagram for explaining a construction for performing a beamforming process based on a batch procedure according to an embodiment of the present invention.

FIG. 10 shows an example of such a construction in which the beamforming for signals originating from different received signals groups is performed in such a manner that the read-out from the memory devices (RAM) 2070 and 2071 is made separately in plural times. In FIG. 10, reference numerals 10010 to 1001v denote parallel received signals for the first read-out and consequential beamforming, and numerals 10020 to 1002v denote parallel received signals for the second read-out and consequential beamforming.

Each of beamformer (BF) units 10030 to 1003v performing the frequency shift and the band selection based on compression, delay and frequency shift and showing the whole of the construction shown in FIG. 2 has real and imaginary outputs. The real outputs and the imaginary outputs of the beamformer (BF) units 10030 to 1003v are inputted to adders 10040 and 10041 by which the results of time shift and phase correction for carrier made corresponding to a receiving focal point in the test body are added for real signals and for imaginary signals. A selector (SEL) 10050 or 10051 makes the selection of whether the output of the adder 10040 or 10041 should be supplied to a memory device (RAM) 10060 or 10061 for writing thereinto or to a gate 10072 or 10073.

A signal read from the memory device (RAM) 10060 or 10061 is supplied to a gate 10070 or 10071. The outputs of the gates 10070 to 10073 are inputted to adders 10080 and 10081 which ultimately output a pair of real and imaginary signals. Signals from the beamformer (BF) units 10030 to 1003v originating from the parallel received signals 10010 to 1001v for the first read-out and consequential beamforming are stored into the memory devices (RAM) 10060 and 10061 by a control signal (not shown) in accordance with the designation of an output destination by the selectors (SEL) 10050 and 10051.

At this time, the read-out from the memory devices (RAM) 10060 and 10061 is not performed and the gates 10070 to 10073 are all closed by a control signal (not shown). Signals originating from the parallel received signals 10020 to 1002v for the second read-out and consequential beamforming are outputted to the gates 10072 and 10073 by a control signal (not shown) in accordance with the designation of an output destination by the selectors (SEL) 10050 and 10051. At this time, the gates 10070 to 10073 are all opened by a control signal (not shown) so that the read-out from the memory devices (RAM) 10060 and 10061 is performed corresponding to the signals which pass through the gates 10072 and 10073 and are outputted for the second read-out.

Thus, the signals originating from the parallel received signals 10010 to 1001v and the signals originating from the parallel received signals 10020 to 1002v are simultaneously added by the adders 10080 and 10081. In the present embodiment, the received signals from the central part 4 of the electro-acoustic converter 3 in FIG. 11 correspond to the parallel received signals 10010 to 1001v in FIG. 10 and the received signals from the other parts 5 and 6 correspond to the parallel received signals 10020 to 1002v.

Figure 9:
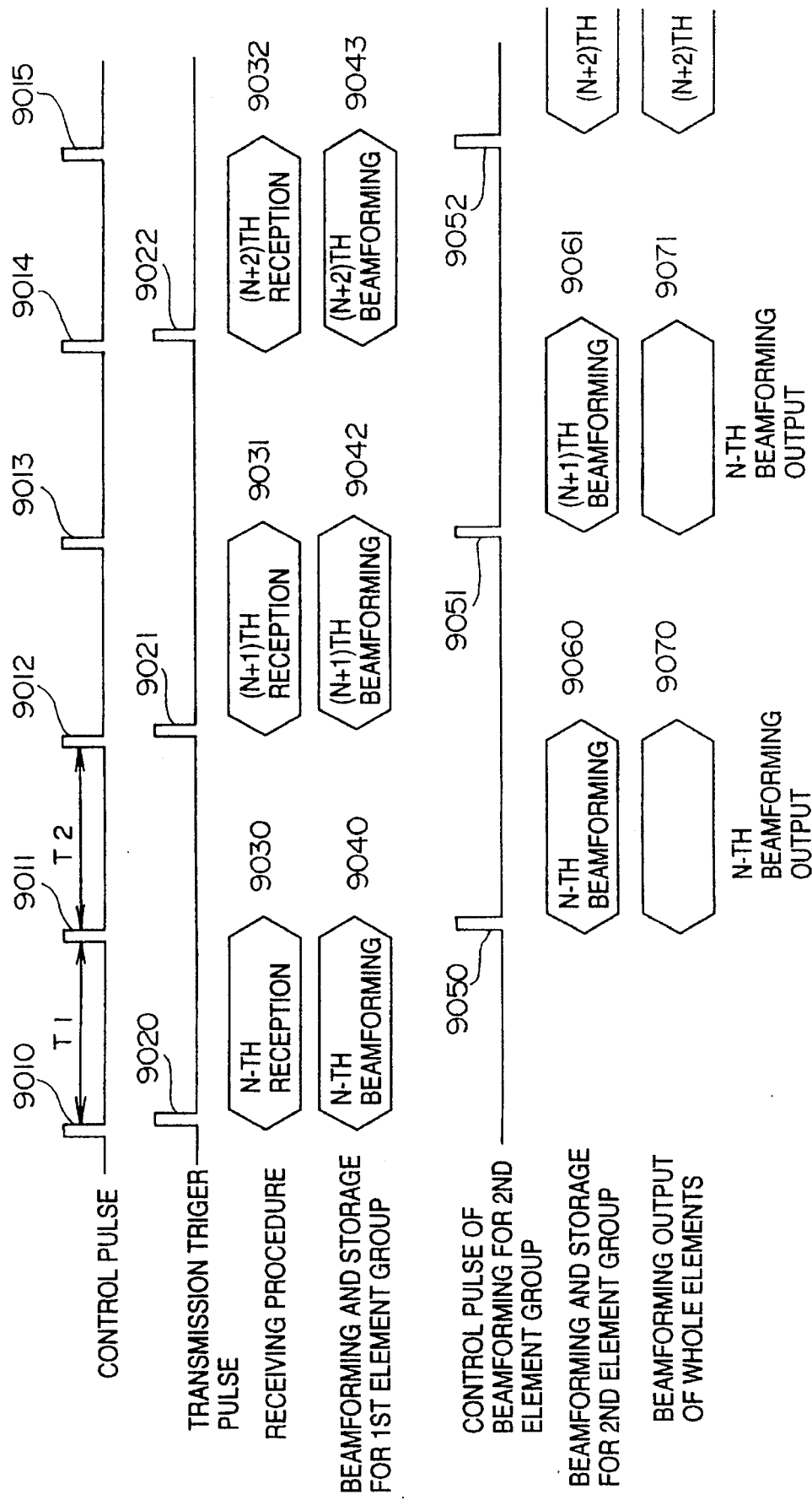
FIG. 9 is a time chart for explaining the beamforming of received signals based on a batch procedure according to an embodiment of the present invention.

FIG. 9 shows a time chart in the case where the beamforming on receiving is performed separately plural times (two times). First, control pulse signals 9010 to 9015 for determining a beamforming sequence are generated. Transmission trigger pulse signals 9020 to 9022 and control pulse signals 9050 to 9052 for beamforming for the second element group are generated on the basis of the control pulse signals 9010 to 9015. Ultrasound waves are transmitted into a testing body in accordance with the transmission trigger pulse signals 9020 to 9022. Immediately thereafter, receiving procedures 9030 to 9032 are started. During the receiving procedure, the beamforming for the first element group (the central part 4 of the electro-acoustic converter 3 in FIG. 11 or the parallel received signals 10010 to 1001v in FIG. 10) and the storage of the result of beamforming into the memory devices (RAM) 10060 and 10061 are made.

Next, the beamforming 9060 or 9061 for the received signals stored in the beamformer units (BF) 10030 to 1003v of FIG. 10 corresponding to the second element group (the end parts 5 and 6 of the electroacoustic converter 3 in FIG. 11 or the parallel received signals 10020 to 1002v in FIG. 10), the read-out of the result of beamforming for the first element group stored in the memory devices 10060 and 10061, and the addition 9070 or 9071 of the result of beamforming for the first element group and the result of beamforming for the second element group are performed in accordance with the control pulse signals 9050 to 9052 for beamforming for the second element group.

It is not required that the periods T1 and T2 of the control pulse signals 9010 to 9015 should be the same. The periods T1 and T2 are optimized in accordance with the processing sequence.

In the case where a high-speed imaging is required, the imaging for only the central part 4 is performed. In the case where the high-speed imaging is not required, the selectors (SEL) 10050 and 10051 shown in FIG. 10 supply the outputs of the adders 10040 and 10041 directly to the gates 10072 and 10073 in accordance with a group of control signals (not shown). At this time, the gates 10070 and 10071 are closed and the gates 10072 and 10073 are opened.

Only the outputs of the adders 10040 and 10041 passed through the gates 10072 and 10073 are inputted to the adders 10080 and 10081. Repeated read-out of data from the beamformer units (BF) 10030 to 1003v is not performed. Thereby, a high-speed imaging is attained.

In a certain case, it is not necessary that the parallel received signals 10020 to 1002v for the second read-out and consequential beamforming should be stored in the beamformer units (BF) 10030 to 1003v over the entire period from a receiving start point of time to a receiving end point of time.

Generally, in many cases, the beamforming for a receiving focal point at a near distance in a certain range is performed with an aperture smaller than the maximum receiving aperture of an electro-acoustic converter. For example, in the case of FIG. 11, an operation is performed in which only the central part 4 is used for a receiving focal point is at a nearer distance than a receiving focal point 1 and the whole of the parts 4, 5 and 6 is used for the receiving focal point 1.

Thus, it is not necessary that parallel received signals which are not used for beamforming should be subjected to analog-digital conversion in the beamformer units (BF) 10031 to 1003v. It is only necessary that the frequency shift, the band compression and the storage into the memory devices should be performed from the point of time when the beamforming is required. Accordingly, for example, in the case where the length of parallel received signals for the second read-out and consequential beamforming is shorter than the length of signals used for the first read-out, the length of signals for the second read-out and consequential beamforming suffices as the capacity of the memory device (RAM) 10060 or 10061 shown in FIG. 10. At this time, it is required that the capacity of the memory device (2070 or 2071 in FIG. 2) in the beamformer units (BF) 10030 to 1003v should be equal to the length of signals for the second read-out and consequential beamforming or larger than that.

According to the above embodiment, an ultrasound signal processor capable of compressing a plurality of parallel received ultrasound input signals on a frequency axis and demodulating them with the plural use of the same signal portion taken into consideration can be realized with a reduced number of constituent elements.

(Embodiment 3)

Next, an embodiment of the construction of the beamformer units (BF) 10030 to 1003v of FIG. 10 different from that shown in FIG. 2 will be explained using FIG. 3.

Received signals 3000 and 3001 are inputted to analog-digital converters (A/D) 3010 and 3011. The succeeding signal processing in FIG. 3 is performed by a digital signal processing. The outputs of the analog-digital converters 3010 and 3011 are inputted to multipliers 3020 to 3023 and are multiplied therein by reference signals 3024 and 3025 and a version thereof through a sign inverter 3026 to make complex frequency shift. A construction for the processing from the input of the received analog signals to the first frequency shift is the same as that in FIG. 2. The complex signal outputs of the multipliers 3020 and 3021 are inputted to selectors (SEL) 3030 and 3031 which operate in accordance with a control signal (not shown). The outputs of the selectors (SEL) 3030 and 3031 are inputted to low-pass filters 3040 and 3041. The complex signal outputs of the multipliers 3022 and 3023 are inputted to low-pass filters 3042 and 3043.

The outputs of the low-pass filters 3042 and 3043 are inputted to selectors (SEL) 3032 and 3033 which operate in accordance with a control signal (not shown). The outputs of the selectors (SEL) 3032 and 3033 are inputted to a complex multiplier 3050. The complex multiplier 3050 makes complex multiplication by reference signals 3051 and 3052 so that a signal passed through the low pass filter and having a single band centering around the vicinity of the DC position is shifted to another frequency band and a phase difference between the carrier of the received signal and the sampling timing pulse signal of the analog-digital converters 3010 and 3011 is corrected. The real and imaginary outputs of the complex multiplier 3050 are inputted to the selectors (SEL) 3030 and 3031 and gates 3070 and 3071, respectively. On the basis of a control signal (not shown), the gates 3070 and 3071 determine whether or not the complex outputs of the complex multiplier 3050 should be inputted to adders 3060 and 3061. The adders 3060 and 3061 add the signals originating from the received signals 3000 and 3001 and having different frequency bands to compress them.

The outputs of the adders 3060 and 3061 are inputted to selector (SEL) 3080 and 3081. In accordance with a control signal (not shown), the selectors (SEL) 3080 and 3081 send the inputted signals directly to resultant outputs 3100 and 3101 or write the inputted signals into memory devices (RAM) 3090 and 3091. The memory device (RAM) 3090 or 3091 provides means for storing the inputted signal and reading it again, thereby enabling an operation of giving a delay to the received signal and an operation of reading the received signal separately plural times.

The outputs read from the memory devices (RAM) 3090 and 3091 provide the resultant outputs 3100 and 3101 when gates 3110 and 3111 on/off-controlled in accordance with a control signal (not shown) are opened.

Next, the function of the construction shown in FIG. 3 will be explained in comparison with that shown in FIG. 2. In the construction shown in FIG. 2, two systems of received signals compressed through the frequency shift are stored in the memory devices (RAM) 2070 and 2071 and one of the two systems of received signals is thereafter read by the complex multiplier 2080 and the low-pass filters 2090 and 2091.

Figure 3:
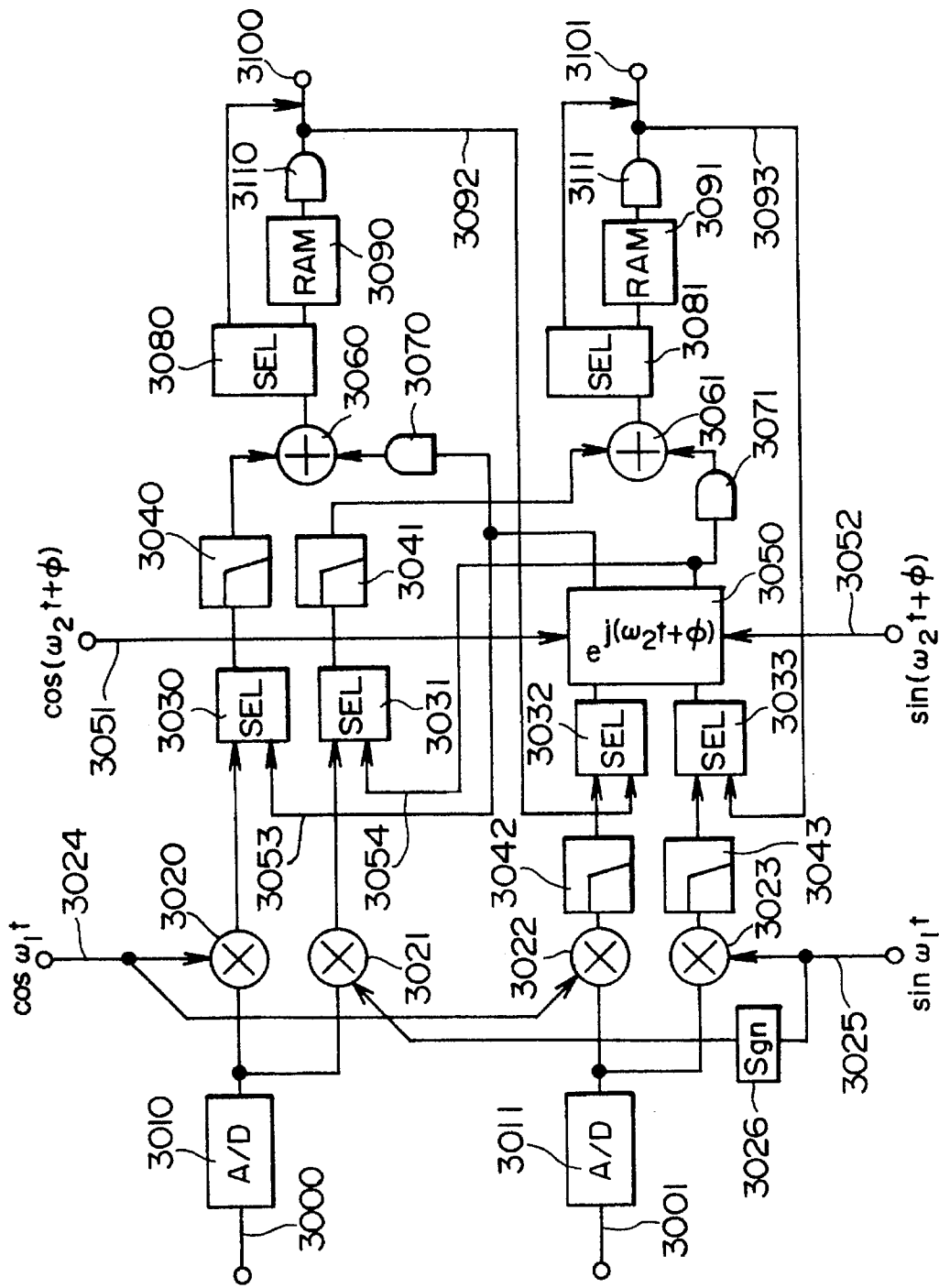
FIG. 3 is a block diagram in the case where the construction of the processor shown in FIG. 2 is further simplified.

On the other hand, in the construction according to FIG. 3, the complex multiplier 2050 and the low-pass filters 2040 and 2041 serve as the complex multiplier 2080 and the low-pass filters 2090 and 2091. Therefore, the embodiment of FIG. 3 is different from the embodiment of FIG. 2 in the provision of a construction in which the outputs of the memory devices (RAM) 2070 and 2071 are selected and are fed back to the inputs of the complex multiplier 2050 again and a construction in which the outputs of the complex multiplier 2050 are fed back to the low-pass filters 2040 and 2041 or 2042 and 2043 in the front stage. In FIG. 3, the outputs of the complex multiplier 2050 are fed back to the low-pass filters 2040 and 2041. However, it is needless to say that the outputs of the complex multiplier 2050 may be fed back to the low-pass filters 2042 and 2043.

In the construction shown in FIG. 3, the compressed signals originating from both the received inputs 3000 and 3001 are stored into the memory devices (RAM) 3090 and 3091 in the receiving procedure. Namely, the selectors (SEL) 3030 to 3033 select as their inputs a group of signals originating from the outputs of the multipliers 3020 to 3023 in accordance with control signals (not shown).

The gates 3070 and 3071 are opened so that signals passed through the low-pass filters 3040 and 3042 and originating from the received input 3000 and signals passed through the complex multiplier 3050 and originating from the received input 3001 are stored into the memory devices (RAM) 3090 and 3091 through the adders 3060 and 3061 and the selectors (SEL) 3080 and 3081. Also, outputs read from the memory devices (RAM) 3090 and 3091 in compliance with a predetermined delay process are passed through the gates 3110 and 3111 brought into opened conditions by control signals (not shown). The passed signals are added together with such signals outputted from other beamformer units. This operation of addition corresponds to adders such as 10040 and 10041 shown in FIG. 10. Next, signals originating from the received input 3001 are read from the memory devices (RAM) 3090 and 3091. In order that this output is shifted again to a frequency band in the vicinity of the DC position through frequency shift by the complex multiplier 3050 as in the case of the signal originating from the received input 3000, the selectors (SEL) 3032 and 3033 select as their inputs the feed-back inputs from the memory devices (RAM) 3090 and 3091.

At this time, the gates 3070 and 3071 are closed and the selectors (SEL) 3030 and 3031 select as their inputs the outputs of the complex multiplier 3050. The outputs of the low-pass filters 3040 and 3041 are inputted to the adders 3060 and 3061. However, the other input of each of the adders 3060 and 3061 is 0 since the gates 3070 and 3071 are closed. The outputs of the adders 3060 and 3061 are sent by the selectors (SEL) 3080 and 3081 to the resultant outputs 3100 and 3101. Thus, two systems of received signals are beamformed with the operation of read-out from the memory devices (RAM) 3090 and 3091 being performed two times.

(Embodiment 4)

Figure 12:
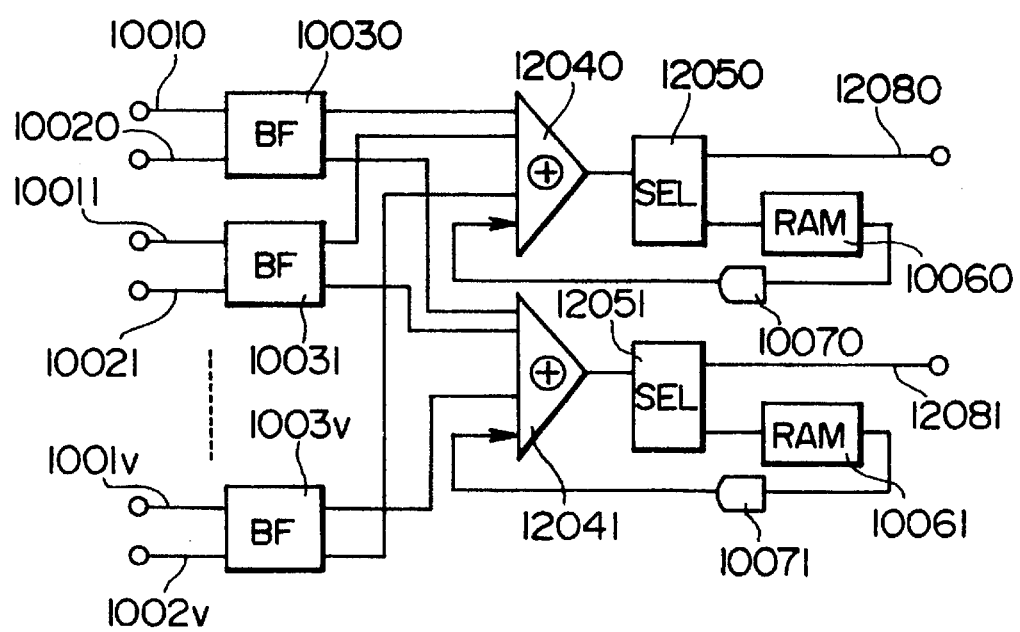
FIG. 12 is a block diagram for explaining another example of the construction for beamforming based on batch procedure having a function similar to that of the construction shown in FIG. 10.

Next, another example of the construction of the beamformer units (BF) 10030 to 1003ν shown in FIG. 10 will be explained using FIG. 12. In FIG. 12, the outputs of beamformer units (BF) 10030 to 1003ν are inputted to adders 12040 and 12041 for real and imaginary signals. Selectors (SEL) 12050 and 12051 select the output destination of the result of the first beamforming so that the result is stored into memory devices (RAM) 10060 and 10061. At this time, gates 10070 and 10071 are closed in accordance with a control signal (not shown). In performing the second beamforming, the results of read-out from the memory devices (RAM) 10070 and 10071 are fed back to the inputs of the adders 12040 and 12041 and are added by the adders 12040 and 12041 together with signals which are newly read from the beamformer units (BF) 10030 to 1003ν. Sides opposite to the memory device sides are selected by the selectors (SEL) 12050 and 12051 so that the results of addition by the adders 12040 and 12041 provide resultant outputs 12080 and 12081.

(Embodiment 5)

In the foregoing embodiments, the beamforming process is realized by an operation in which after the received signals have been compressed and stored in the memory devices, the received signals are read from the memory devices separately plural times. Next, there will be shown an embodiment in which the beamforming is performed in such a manner that signals compressed in memory devices and originating from different received signal groups are read by a time sharing procedure. The different received signal groups indicate received signal groups held into different frequency bands at a signal band compressing procedure.

Figure 13:
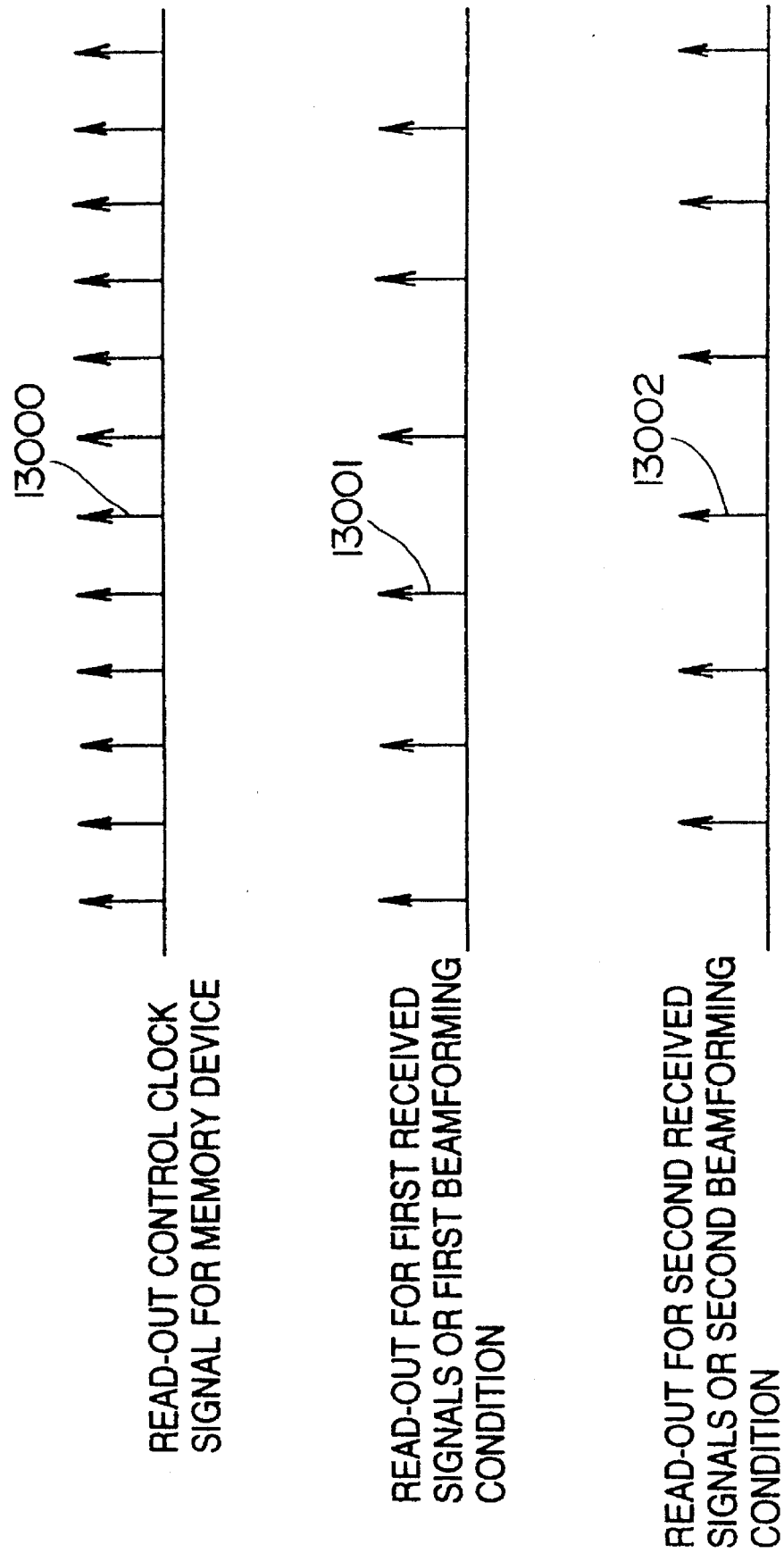
FIG. 13 is a time chart for explaining a time sharing procedure for read-out.

As shown in FIG. 13, a read-out control clock signal 13000 for memory device is time-shared to generate two phases of clock signals 13001 and 13002. The clock signal 13001 corresponds to the read-out for a first group of received signals, and the clock signal 13002 corresponds to the read-out for a second group of received signals.

The clock signal 13001 and the clock signal 13002 are obtained by dividing the read-out control clock signal 13000 for memory device. Signal values are successively read from memory devices corresponding to beamforming conditions (such as delay time and phase correction amount) characteristic of the first and second received signal groups.

For example, in the case where the memory device is a RAM, a delay process under the characteristic condition is possible maintaining a sampling period possessed by signal values written in the memory device. Namely, though a read-out period for each received signal group is two times as long as the period of read-out from the memory device, the precision of the delay time can be maintain a high sampling period at the point of time of writing without being deteriorated.

Figure 14:
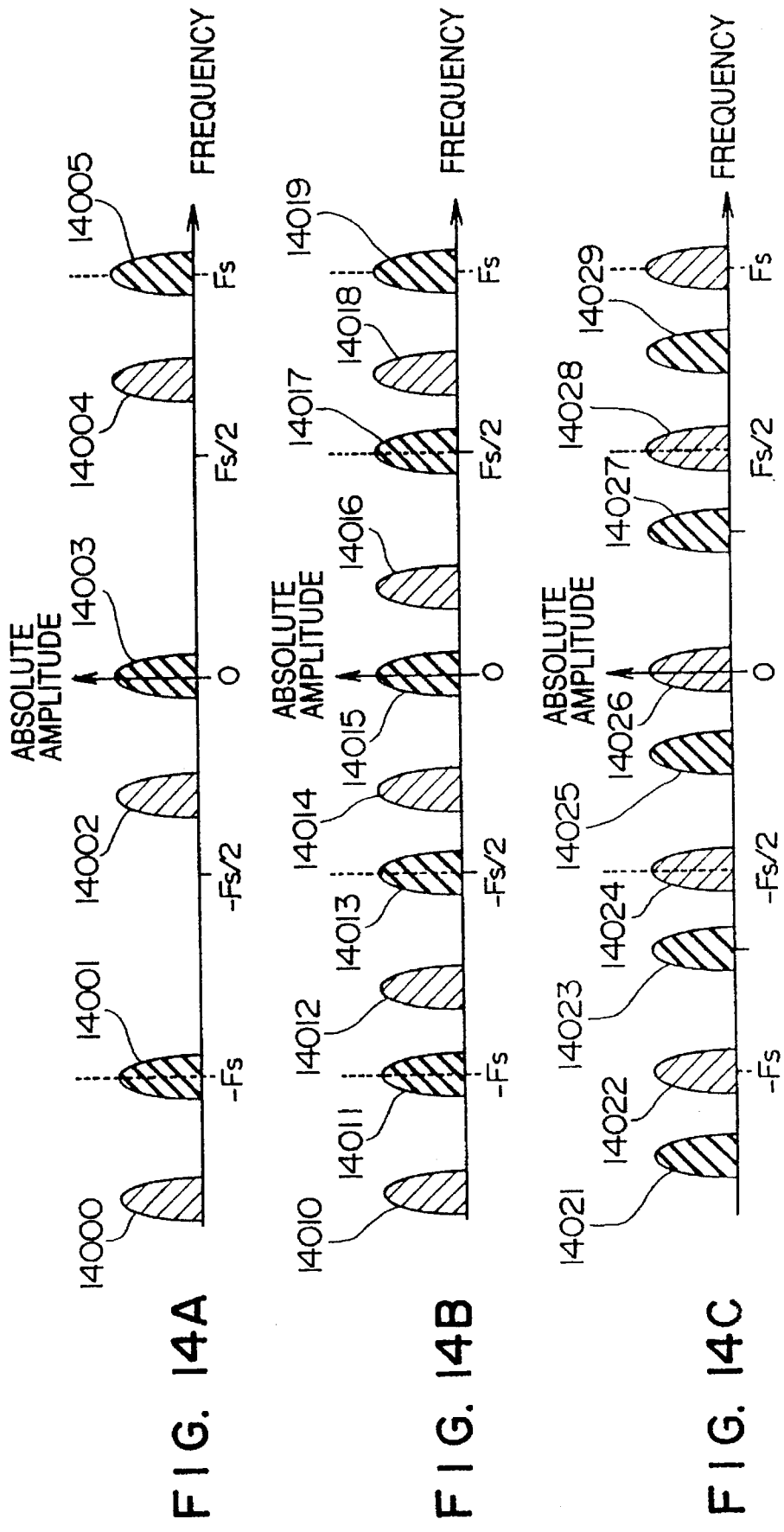
FIGS. 14A to 14C are spectral diagrams for explaining band shift after the time sharing procedure.
Figure 15:
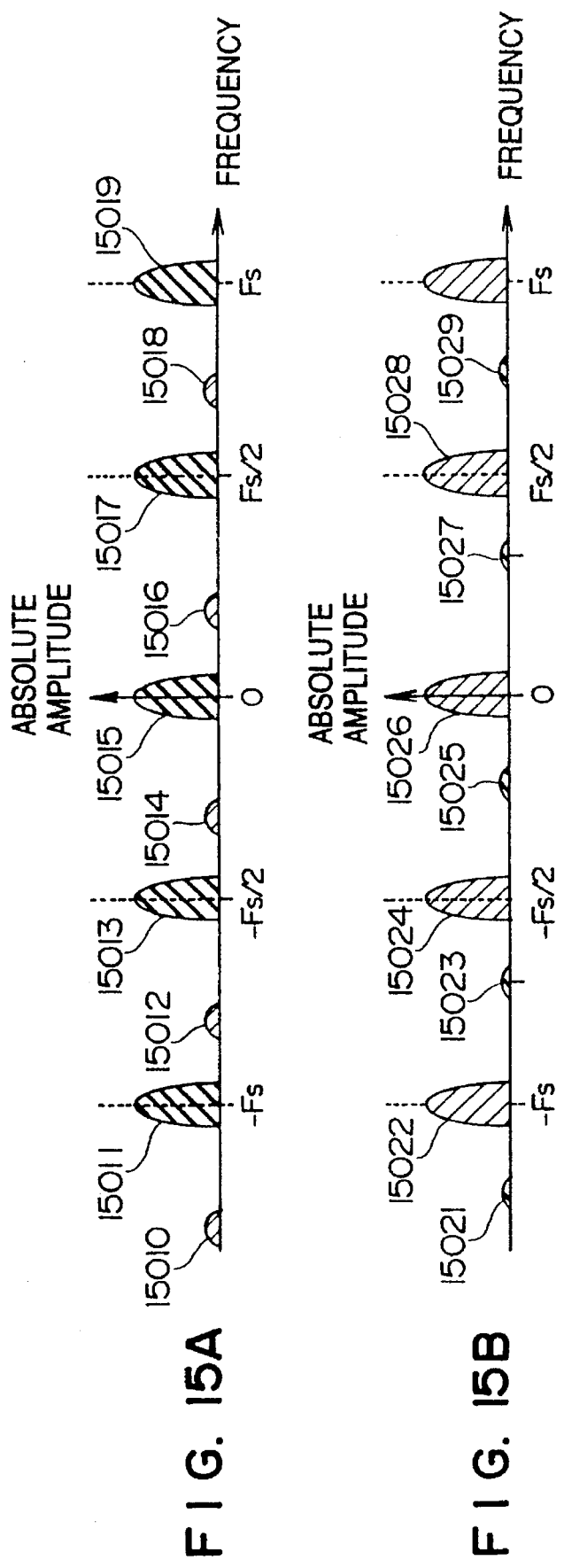
FIGS. 15A and 15B are spectral diagrams for explaining demodulation after the time sharing procedure.

The change of a frequency spectrum caused by the time sharing procedure will be explained using FIGS. 13A to 14D and FIGS. 15A and 15B. FIG. 14A shows the frequency spectrum of two received signal groups stored in memory devices with band compressed. The frequency spectrum of FIG. 14A shows only bands of FIG. 6D other than the bands 601a, 603a, 605a, 622a, 624a and 626a which are regarded as being sufficiently attenuated. Bands 14000 to 14005 shown in FIG. 14A are subjected to a time sharing procedure so that the reflection is made around a frequency which is one half of the sampling frequency Fs. There results in bands 14010 to 14019 shown in FIG. 14B.

When the signal shown in FIG. 14B is frequency-shifted in a negative direction by use of a complex multiplier, the bands 14011 to 14019 shown in FIG. 14B are shifted resulting in bands 14021 to 14029 shown in FIG. 14C. If a low-pass filter is used, the band 14015 or 14026 in the vicinity of the DC position is ultimately obtained. With a proper low-pass filter, the bands 14010 to 14019 shown in FIG. 14B turn into bands 15010 to 15019 shown in FIG. 15A.

Similarly, the bands 14021 to 14029 shown in FIG. 14C turn into bands 15021 to 15029 shown in FIG. 15B. Even if such a processing is performed, the use of a RAM as the memory device provides a merit that the time (or phase) precision at the original sampling period can be maintained.

Next, the specific construction of the present embodiment for performing the time sharing procedure will be explained using FIG. 16. The construction of FIG. 16 concerning a process until the storage of signals into memory devices (RAM) 2070 and 2071 with band compressed is the same as that shown in FIG. 2.

Received signals are successively read from the memory devices (RAM) 2070 and 2071 in a time sharing manner and corresponding to different beamforming conditions and are then inputted to a complex multiplier 2080.

The complex multiplier 2080 performs frequency shift and phase correction. But, since signals corresponding to the different beamforming conditions are alternately inputted from the memory devices (RAM) 2070 and 2071, reference signals 2081 and 2082 to the complex multiplier 2080 are inputted as signals corresponding to the different beamforming conditions in synchronism with the input from the memory devices.

The outputs of the complex multiplier 2080 are sampled by samplers 16000 and 16001 for real signals and samplers 16002 and 16003 for imaginary signals. At this time, the samplers 16000 and 16001 perform the sampling alternately. The same holds for the samplers 16002 and 16003. The sampler 16000 is synchronous with the sampler 6002.

The samplers 16000 to 16003 outputs sampled values to the succeeding low-pass filters 16010 to 16013. As required, the sampler may output the sampled value and 0 alternately or two identical sampled values continuously. Only a band having its center frequency in the vicinity of the DC position is passed through each of the low-pass filters 16010 to 16013. The outputs of the filters are inputted to selectors (SEL) 16020 and 16021. The selectors (SEL) 16020 and 16021 select the outputs of the filters alternately for the provision of a time sharing output, thereby providing resultant outputs 16030 and 16031.

Figure 16:
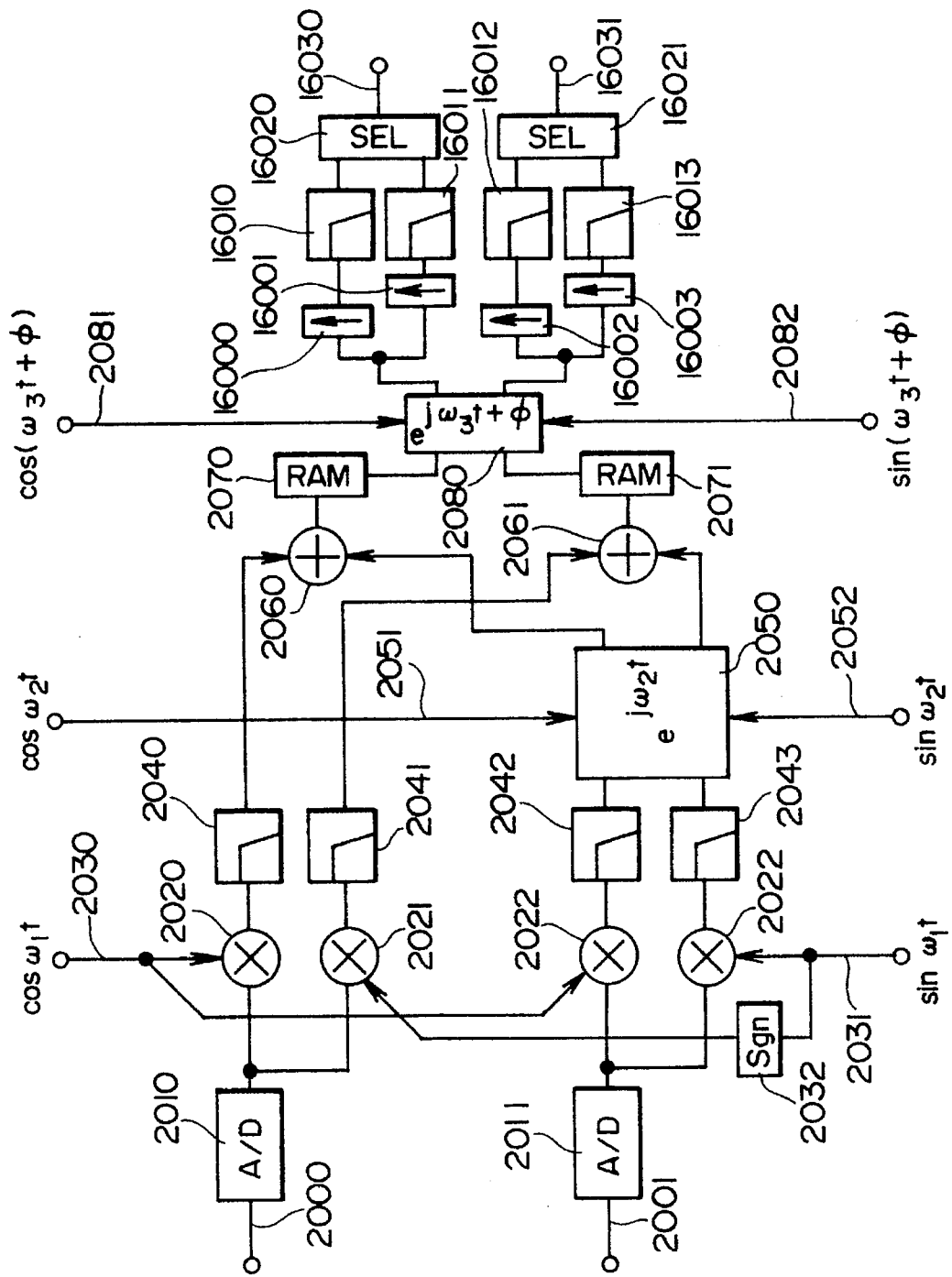
FIG. 16 is a block diagram for explaining a construction which realizes the demodulation after the time sharing procedure.

The whole of FIG. 16 forms one beamformer unit or the constituent unit of a beamformer. A plurality of such beamformer units are provided to form a beamforming section so that time sharing signal outputs for each of real and imaginary signals are added to perform the beamforming.

According to the time sharing procedure in the present embodiment, the beamforming performed with a signal processing (or batch procedure) made plural times in the case of the second to fourth embodiments can be performed at a time, thereby shortening a time required for a beamforming process to improve the imaging speed.

(Embodiment 6)

In the fifth embodiment, there is realized a beamforming process in which compressed reception signals in memory devices are read in a time sharing manner so that signals originating from different received signal groups are alternately processed. However, a time sharing procedure is also possible in such a manner that signals originating from the same received signal group are read under different beamforming conditions.

In the the case of a sixth embodiment which will now be mentioned, a time sharing procedure for signals originating from one of different received signal groups is followed by a time sharing procedure again. The reflection of a frequency spectrum by the time sharing procedure, the frequency shift and the filtering effect are the same as those explained in conjunction with FIGS. 14 and 15 in the fifth embodiment.

As shown in FIG. 13, a read-out control clock signal 13000 is time-shared to generate two phases of clock signals 13001 and 13002. In the present embodiment, however, the clock signals 13001 and 13002 correspond to different beamforming conditions for the same received signal group.

As in the case of the fifth embodiment, the use of a RAM as the memory device enables a delay process under the characteristic condition while maintaining a sampling period possessed by signal values written in the memory device. The construction of a beamformer unit is the same as that shown in FIG. 16 but the reference signal inputs 2081 and 2082 correspond to the different beamforming conditions for the same received signal group. Further, the construction of FIG. 10 or 12 provided with the memory devices (RAM) 10060 and 10061 is used in order to make the addition by a beamforming output for the different received signal groups.

With the above construction, an approximately doubled beamforming process time required in the case where a beamforming process for two received signal groups is performed separately two times, can be cancelled in such a manner that processes for two different receiving focal points are simultaneously performed in a time sharing manner. Namely, a beamforming process performed while conducting an ultrasound transmitting and receiving process twice is replaced by a receiving and beamforming process of two times simultaneously performed for an untrasound transmitting process conducted once, thereby enabling a high-speed operation or cancelling the increase of a processing time caused in the case where a beamforming process for two received signal groups inputted at a time is performed separately twice.

(Embodiment 7)

The fifth embodiment has shown the example in which different received signal groups are subjected to a time sharing procedure, and the sixth embodiment has shown the example in which the same received signal group is subjected to a time sharing procedure. In a seventh embodiment which will now be mentioned, received signals stored in memory devices are read at a frequency twice as high as that at the time of writing to perform a four-phase time sharing procedure.

Figure 17:
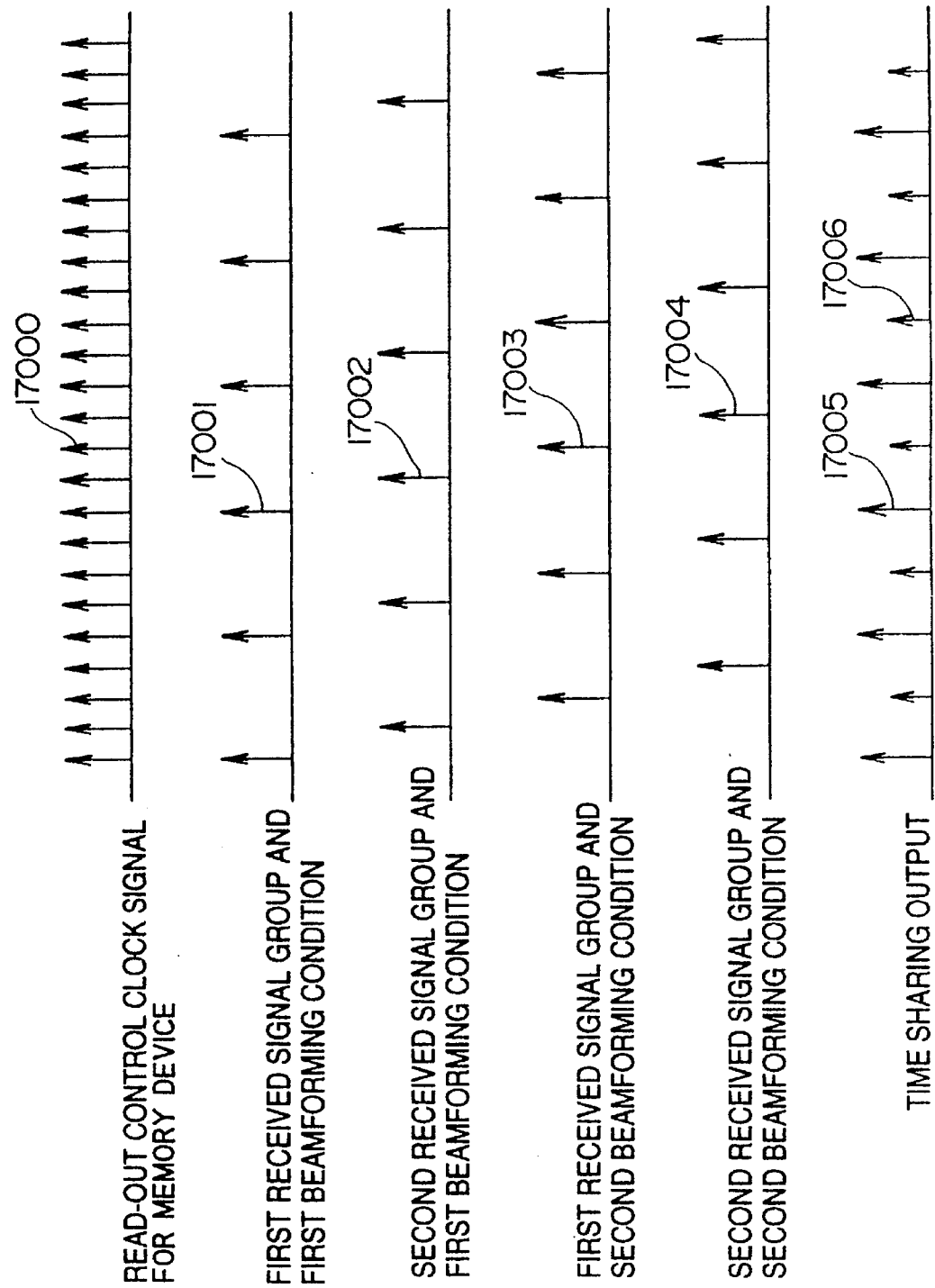
FIG. 17 is a time chart for explaining a time sharing procedure for a beamforming process performed for a plurality of received signal groups and a plurality of beamforming conditions.

The four-phase time sharing procedure is realized in such a manner that the read-out from the memory devices is made using a two-phase clock signal based on the rise and fall of clocks used for the sampling at the time of analog-digital conversion of received signal and the reading operation is performed two times within the period of writing in the memory device. A relationship between clocks is shown in FIG. 17.

Clock signals 17001 and 17002 of those into which a read-out control clock signal 17000 as a reference clock signal is divided are used for the read-out of received signals according to a first beamforming condition, and clock signals 17003 and 17004 thereof are used for the read-out of received signals according to a second beamforming condition.

Also, the clock signals 17001 and 17003 correspond to the read-out of a group of first received signals and the clock signals 17002 and 17004 correspond to the read-out of a group of second received signals. In order that the first received signal group and the second received signal group are added under the same beamforming condition (for example, the condition that a receiving focal point is the same), there are used four phases which include two phases in the former half and two phases in the latter half.

Thus, two groups of signals are added beforehand and signal groups corresponding to different beamforming conditions are outputted separately in a time sharing manner. This situation is indicated by 17005 and 17006. The long arrow 17005 represents the output under the first beamforming condition and the short arrow 17006 represents the output under the second beamforming condition.

Figure 18:
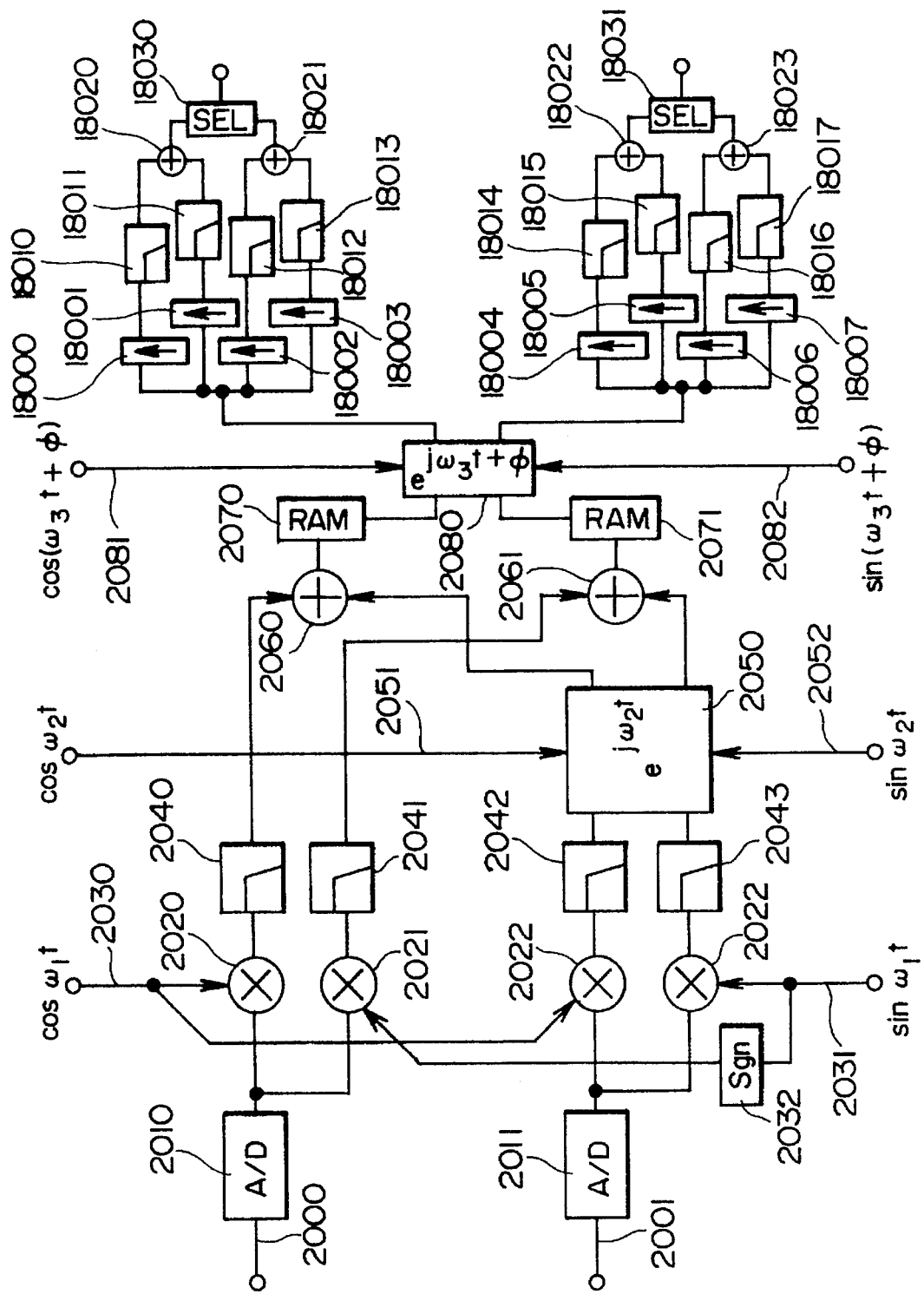
FIG. 18 is a block diagram showing a construction for realizing the time sharing procedure shown in FIG. 17.

Next, the specific construction of the present embodiment for performing a time sharing procedure will be shown using FIG. 18. The construction of FIG. 18 concerning a process until the storage of signals into memory devices (RAM) 2070 and 2071 with band compressed is the same as that shown in FIG. 2. Received signals are successively read from the memory devices (RAM) 2070 and 2071 in a four-phase time sharing manner and corresponding to different beamforming conditions and different received signal groups and are then inputted to a complex multiplier 2080.

The complex multiplier 2080 performs frequency shift and phase correction. But, since signals corresponding to the different beamforming conditions are inputted from the memory devices (RAM) 2070 and 2071, reference signals 2081 and 2082 to the complex multiplier 2080 are inputted as signals corresponding to the different beamforming conditions in synchronism with the input from the memory devices. The output of the complex multiplier 2080 are sampled by samplers 18000 to 18003 for real signals and samplers 18004 to 18007 for imaginary signals. At this time, the samplers 18000 to 18003 for real signals perform the sampling sequentially. The same holds for the samplers 18004 to 18007. The samplers 18000 and 18004 are synchronous with each other. The same holds for the samplers 18001 and 18005, the samplers 18002 and 18006, and the samplers 18003 and 18007.

The samplers 18000 to 18007 outputs sampled values to the succeeding low-pass filters 18010 to 18017. As required, the sampler may output the sampled value and 0 alternately or two identical sampled values continuously. Only a band having its center frequency in the vicinity of the DC position is passed through each of the low-pass filters 18010 to 18017.

The outputs of the filters 18010 to 18017 are inputted to adders 18020 to 18023. In order that first and second received signal groups shifted by one clock are added, each of the low-pass filters 18010, 18012, 18014 and 18016 provides its output delayed by one clock. The outputs of the adders 18020 to 18023 are inputted to selectors (SEL) 18030 and 18031. The selectors (SEL) 18030 and 18031 select the outputs of the filters alternately for the provision of a time sharing output, thereby providing resultant outputs.

The whole of FIG. 18 forms one beamformer unit or the constituent unit of a beamformer. A plurality of such beamformer units are provided to form a beamforming section so that time sharing signal outputs for each of real and imaginary signals are added to perform the beamforming.

According to the time sharing procedure in the present embodiment, the beamforming performed with a signal processing or batch processing conducted plural times in the case of the second to fourth embodiments can be performed at a time and the beamforming for different beamforming conditions (such as different receiving focal points) can be performed at a time, thereby improving the imaging speed.

Further, since the number of signals to be subjected to a parallel beamforming process and the number of beamforming conditions can be increased without increasing the sampling frequency of the analog-digital converter, there is no problem that the electric S/N ratio (or the number of effective bits) of the analog-digital conversion is decreased and it is possible to avoid a problem that the number of input signals obtained through a receiving process performed once is increased so that the storage capacity of the memory device is increased to a more capacity than that required.

Figure 4:
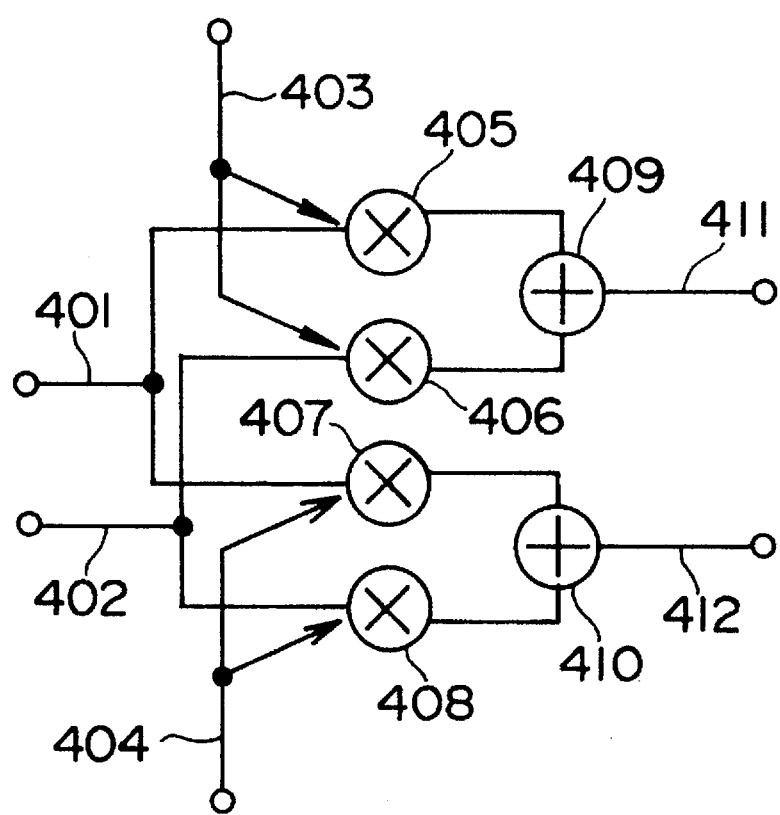
FIG. 4 is a diagram showing the construction of a complex multiplier or complex frequency mixer according to an embodiment of the present invention.

The construction of the complex multiplier used in the first to seventh embodiments is shown in FIG. 4. An in-phase (or real) input 401 and a quadrature (or imaginary) input 402 are inputted to multipliers 405 and 06 which in turn perform the multiplication by reference signals 403 and 404. The outputs of the multipliers 405 to 408 are added by adders 409 and 410 for real and imaginary signals. In the case where the reference signal 404 is an imaginary reference signal part, it is required that the output of the multiplier 408 should be sign-inverted or the adder 410 subtracts the output of the multiplier 408 from the output of the multiplier 407. Reference numeral 411 denotes the output of the adder 409 and numeral 412 denotes the output of the adder 410.

Figure 8:
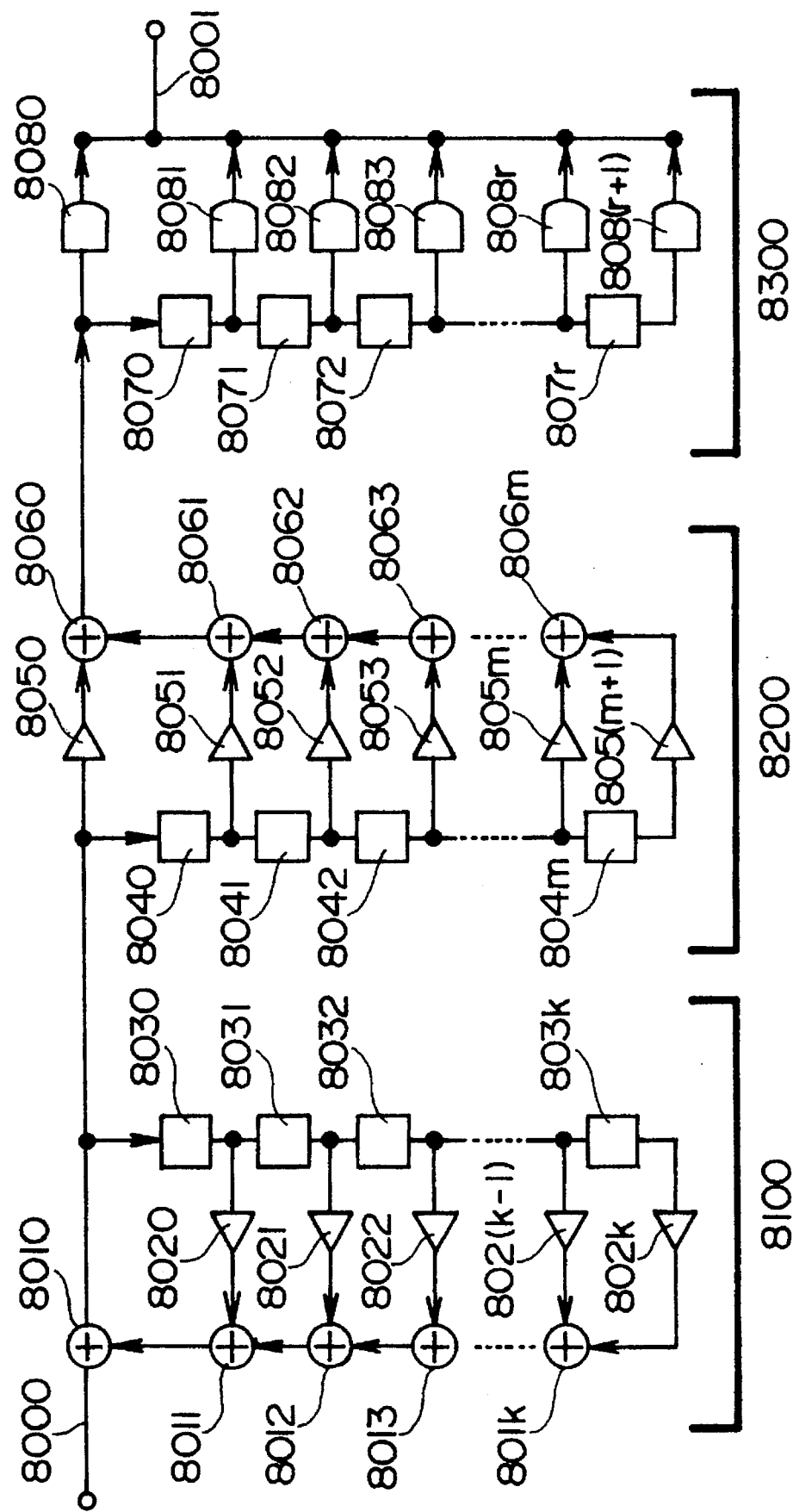
FIG. 8 is a diagram for explaining the digital circuit construction of a low-pass filter according to an embodiment of the present invention.

The construction of the low-pass filter used in the first to seventh embodiments is shown in FIG. 8. The low-pass filter is composed of three blocks which include a feed-back section 8100, a feed-forward section 8200 and a timing controller 8300.

In the feed-back section 8100, time series data successively delayed by unit delay devices 8030 to 803$k$ is subjected to the multiplication by predetermined coefficients in coefficient multipliers 8020 to 802$k$ and to the successive addition by adders 8011 to 802$k$ and is then fed back by an adder 8010. In the feed-forward section 8200, time series data successively delayed by unit delay devices 8040 to 804$m$ is subjected to the multiplication by predetermined coefficients in coefficient multipliers 8050 to 805$(m+1)$ and to the successive addition by adders 8061 to 806$m$ and is then outputted by an adder 8060 to the timing controller 8300. In the timing controller 8300, time series data successively delayed by unit delay devices 8070 to 807$r$ is outputted through the on/off operation of gates 8080 to 808$(r+1)$ as a resultant output 8001.

The sequence of arrangement of the blocks 8100, 8200 and 8300 is not limited to that shown in FIG. 8. Also, a part of these blocks can be omitted in accordance with the purpose.

(Embodiment 8)

Figure 19:
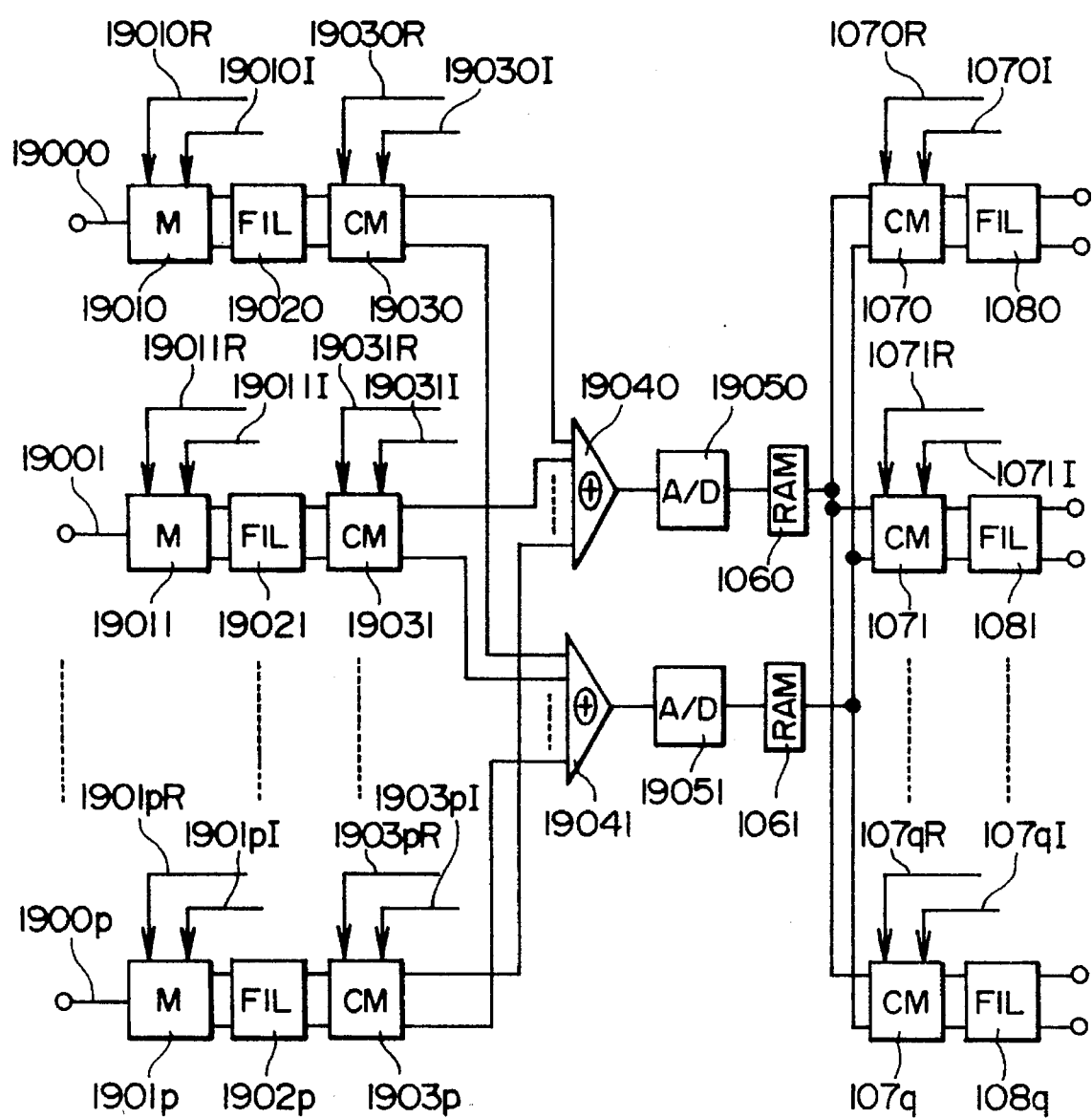
FIG. 19 is a block diagram in the case where a signal band compressing procedure in the construction shown in FIG. 1 is performed by an analog signal processing.

The construction of another embodiment of the present invention is shown in FIG. 19. The construction shown in FIG. 19 provides an example in which the construction of FIG. 1 in front of the memory devices (RAM) 1060 and 1061 is realized by an analog signal processing. Received ultrasound signals 19000, 19001, and 1900$p$ are inputted to frequency mixers (M) 19010, 19011, - - - and 1901$p$. The frequency mixers 19010, 19011, - - - and 1901$p$ perform frequency shift by use of reference sine signals 19010R, 19011R, - - - and 1901$p$R and reference cosine signals 19010I, 19011I, - - - and 1901$p$I. The outputs of the frequency mixers 19010, 19011, - - - and 1901$p$ are inputted to low-pass filters (FIL) 19020, 19021, - - - and 1902$p$. The outputs of the low-pass filters 19020, 19021, - - - and 1902$p$ are orthogonal or quadrature detection outputs and are inputted to complex frequency mixers (CM) 19030, 19031, - - - and 1903$p$ so that frequency shift is performed again.

The complex frequency mixers 19030, 19031, - - - and 1903$p$ perform frequency shift again by use of reference sine signal inputs 19030R, 19031R, - - - and 1903$p$R and reference cosine signal inputs 19030I, 19031I, - - - and 1903pl. The outputs of the complex frequency mixers 19030, 19031, - - - and 1903p are amplified by amplifiers (not shown) and are then inputted to adders 19040 and 19041 with level-matching made between the parallel received signals.

The outputs of the adders 19040 and 19041 are inputted to analog-digital converters (A/D) 19050 and 19051. It is required that a sampling frequency at this time should be about two to four times as high as the frequency of an output signal band of the adders 19040 and 19041. The outputs of the analog-digital converters 19050 and 19051 are stored into memory devices (RAM) 1060 and 1061. The succeeding construction is the same as that in FIG. 1 and a realizable function is similar to those in the second to seventh embodiments. Also, it is needless to say that in order to increase the sampling frequency of the analog-digital converters 19050 and 19051, the analog-digital converters themselves can be parallel-arranged to perform a sampling in a time sharing manner.

It is needless to say that the foregoing embodiments merely show specific examples of the present invention and the present invention is not limited to the disclosed embodiments.

We claim:

1. An ultrasound signal processor comprising:
   an electro-acoustic transducer array for receiving ultrasound signals from a testing body to obtain a plurality of received analog signals which are electric signals;
   analog-digital converters for sampling at least two of said plurality of received analog signals;
   multipliers for performing a multiplication of the outputs of said analog-digital converters and first complex digital reference signals;
   first low-pass filters for limiting the signal bands of the outputs of said multipliers;
   first complex multipliers for performing a multiplication of second complex digital reference signals and the outputs of said first low-pass filters;
   adders for performing an addition of the outputs of said first complex multipliers for real signals and an addition thereof for imaginary signals;
   memory devices for storing the outputs of said adders;
   second complex multipliers for performing a multiplication of signals read from said memory devices and third complex digital reference signals;
   second low-pass filters for limiting the signal bands of the outputs of said second complex multipliers; and
   a signal processing circuit for converting signals read from said second low-pass filters into an image signal concerning information of the interior of said testing body.

2. An ultrasound signal processor according to claim 1, wherein the number of said first complex multipliers parallel-arranged and the number of said second complex multipliers parallel-arranged are smaller than the number of said received signals by one.

3. An ultrasound signal processor according to claim 1, further comprising samplers for enabling a time sharing procedure in a construction preceding said memory devices, third low-pass filters additionally provided in said construction preceding said memory devices corresponding to the total of parallel process increased due to said time sharing procedure, and selectors for outputting the outputs of said third low-pass filters in a time sharing manner.

4. An ultrasound signal processor according to claim 3, further comprising adders for partially adding the outputs of said third low-pass filters which precede said samplers for performing said time sharing procedure.

5. An ultrasound signal processor according to claim 1, wherein constructions for performing a frequency shift and addition of said received signals is formed by analog circuits and signals output by said constructions are input to the analog-digital converters.

6. An ultrasound signal processor according to claim 1, wherein the signals stored in said memory devices are read and added through a batch processing performed plural times.

7. An ultrasound signal processor according to claim 3, wherein signals originating from received signals having different bands are successively read from said memory devices through a time sharing procedure.

8. An ultrasound signal processor according to claim 3, wherein signals originating from received signals having the same band are successively read from said memory devices under different beamforming conditions through a time sharing procedure.

9. An ultrasound signal processor according to claim 3, wherein signals originating from received signals having the same band are read from said memory devices under M-different beamforming conditions through a MxN-times sharing procedure and simultaneously signals originating from received signals having N-different bands are added in the time sharing procedure, thereby reducing the number of time sharing processes for output to M, where M and N are integers.

10. An ultrasound signal processor comprising:
    an electro-acoustic transducer array for receiving ultrasound signals from a testing body to obtain a plurality of received analog signals which are electric signals;
    analog-digital converters for sampling at least two of said plurality of received analog signals;
    multipliers for performing a multiplication of the outputs of said analog-digital converters and first complex digital reference signals;
    first low-pass filters for limiting the signal bands of the outputs of said multipliers, said limited bands being provided on first outputs of said first low-pass filters;
    first complex multipliers for performing a multiplication of second complex digital reference signals and the first outputs of said first low-pass filters;
    adders for performing an addition of the outputs of said first complex multipliers for real signals and an addition thereof for imaginary signals;
    memory devices for storing the outputs of said adders;
    selectors for signal selection for providing outputs of said memory devices to second inputs of said first complex multipliers and second outputs of said first low-pass filter for providing second low-pass filter outputs; and
    a signal processing circuit for converting the second low-pass filter outputs into an image signal concerning information of the interior of said testing body.

* * * * *